(12) United States Patent
Salamone et al.

(10) Patent No.: US 11,839,626 B2
(45) Date of Patent: Dec. 12, 2023

(54) COMPOSITION AND KITS FOR INHIBITION OF PATHOGENIC MICROBIAL INFECTION AND METHODS OF USING THE SAME

(71) Applicant: ROCHAL INDUSTRIES, LLC, San Antonio, TX (US)

(72) Inventors: Joseph Charles Salamone, San Antonio, TX (US); Katelyn Elizabeth Reilly, San Antonio, TX (US); Ronald Thomas Nixon, Sugar Land, TX (US); Ann Beal Salamone, San Antonio, TX (US); Kelly Xiaoyu-Chen Leung, San Antonio, TX (US)

(73) Assignee: ROCHAL TECHNOLOGIES LLC, Fort Worth, TX (US)

( * ) Notice: Subject to any disclaimer, the term of this patent is extended or adjusted under 35 U.S.C. 154(b) by 0 days.

(21) Appl. No.: 15/693,806

(22) Filed: Sep. 1, 2017

(65) Prior Publication Data
US 2017/0360825 A1 Dec. 21, 2017

Related U.S. Application Data

(62) Division of application No. 14/504,079, filed on Oct. 1, 2014, now abandoned.

(51) Int. Cl.
| | |
|---|---|
| *A61K 31/785* | (2006.01) |
| *A61K 45/06* | (2006.01) |
| *A61K 9/00* | (2006.01) |
| *A61P 31/00* | (2006.01) |
| *A61K 9/70* | (2006.01) |
| *A61Q 17/00* | (2006.01) |
| *A01N 25/10* | (2006.01) |
| *A61K 31/23* | (2006.01) |
| *A61K 8/84* | (2006.01) |
| *A61K 8/04* | (2006.01) |
| *A61K 36/61* | (2006.01) |
| *A01N 25/34* | (2006.01) |
| *A61K 8/43* | (2006.01) |
| *A61K 8/9789* | (2017.01) |
| *A01N 47/44* | (2006.01) |
| *A61Q 17/04* | (2006.01) |
| *A61Q 19/00* | (2006.01) |
| *A61Q 17/02* | (2006.01) |

(52) U.S. Cl.
CPC ........... *A61K 31/785* (2013.01); *A01N 25/10* (2013.01); *A01N 25/34* (2013.01); *A01N 47/44* (2013.01); *A61K 8/046* (2013.01); *A61K 8/43* (2013.01); *A61K 8/84* (2013.01); *A61K 8/9789* (2017.08); *A61K 9/0014* (2013.01); *A61K 9/7015* (2013.01); *A61K 31/23* (2013.01); *A61K 36/61* (2013.01); *A61K 45/06* (2013.01); *A61P 31/00* (2018.01); *A61Q 17/005* (2013.01); *A61Q 17/02* (2013.01); *A61Q 17/04* (2013.01); *A61Q 19/005* (2013.01)

(58) Field of Classification Search
CPC .................................................. A61K 31/785
See application file for complete search history.

(56) References Cited

U.S. PATENT DOCUMENTS

| | | |
|---|---|---|
| 4,374,126 A | 2/1983 | Cardarelli |
| 5,103,812 A | 4/1992 | Salamone |
| 5,417,968 A | 5/1995 | Staats |
| 5,916,541 A | 6/1999 | Stewart |
| 6,180,127 B1 | 1/2001 | Calton |
| 6,582,683 B2 | 6/2003 | Jezior |
| 7,622,512 B2 | 11/2009 | Schorzman |
| 7,670,997 B2 | 3/2010 | Burke |
| 7,795,326 B2 | 9/2010 | Salamone |
| 8,263,720 B1 | 9/2012 | Salamone |
| 8,343,523 B2 | 1/2013 | Toreki |
| 2003/0147925 A1 | 8/2003 | Sawan |
| 2004/0259951 A1 | 12/2004 | Clarkson et al. |
| 2007/0048344 A1 | 3/2007 | Yahiaoui |
| 2009/0155451 A1 | 6/2009 | Ylitalo et al. |
| 2010/0187263 A1 | 7/2010 | Lestage et al. |

(Continued)

FOREIGN PATENT DOCUMENTS

| | | |
|---|---|---|
| EP | 0612518 | 9/1997 |
| EP | 1358800 | 11/2003 |

(Continued)

OTHER PUBLICATIONS

Schlievert et al. (Glycerol Monolaurate Antibacterial Activity in Broth and Biofilm Cultures). Jul. 2012.*
Healthline. Necrotizing Fascitits (Soft Tissue Infections). Jul. 2012.*
Misiakos et al. Current Concepts in Management of Necrotizing Fasciitis. Sep. 2014.*
Hakkarainen et al. Necrotizing Soft Tissue Infections: Review and Current Concepts in Treatment, Systems of Care and Outcomes. Aug. 2014.*
Lomax. Amphoteric Surfactants Second Edition. 1996.*

(Continued)

*Primary Examiner* — Sarah Alawadi
(74) *Attorney, Agent, or Firm* — DUANE MORRIS LLP; Gregory M. Lefkowitz; Brandon A. Chan

(57) ABSTRACT

Antimicrobial polymer coating formulations are prepared that protect biological surfaces by treating, reducing, ameliorating, preventing or inhibiting pathogenic microorganism ingress to a human or animal host, reducing the potential for infection, particularly by necrotizing fasciitis originating microorganisms, through use of a polymer coating barrier containing antimicrobial agents that facilitates sustained release of biocidal agents active against such opportunistic microorganisms. Such formulations are effective for inhibiting microbial ingress pertaining to soft tissue and skin tears, abrasions, punctures and surgical wounds, and can be used as in water environments and as a skin protectant sunscreen and insect repellent.

20 Claims, No Drawings

(56) References Cited

U.S. PATENT DOCUMENTS

| | | | |
|---|---|---|---|
| 2011/0076244 A1 | 3/2011 | Hammer | |
| 2012/0016055 A1 | 1/2012 | Chen et al. | |
| 2012/0115812 A1 | 5/2012 | Hammer | |
| 2013/0150451 A1 | 6/2013 | Salamone | |
| 2013/0231302 A1* | 9/2013 | Raad | A61L 2/186 514/54 |
| 2013/0251773 A1 | 9/2013 | Galiatsatos | |
| 2013/0261534 A1 | 10/2013 | Niezgoda | |
| 2014/0127320 A1 | 5/2014 | Salamone | |

FOREIGN PATENT DOCUMENTS

| | | |
|---|---|---|
| EP | 2196225 | 6/2010 |
| EP | 2407028 | 1/2012 |
| WO | 2006/131401 | 12/2006 |

OTHER PUBLICATIONS

Kulp et al. Biological Funcations and Biogenesis of Secreted Bacterial Outer Membrane Vesicles. (Year: 2010).*

Kim et al. Outer Membrane Vesicles of Vibrio Vulnifus Delivery Cytolysin-Hemolysin VvhA into Epithelial Cells to Induce Cytotoxicity. (Year: 2010).*

Pending U.S. Appl. No. 14/046,591, entitled "Non-Self-Adherent Coating Materials."

Sasol, Ethanol SDA 40B 200 Product Specification Version 5a, Sasol Chemicals North America LLC, Retrieved May 2015.

Diversified CPC International, Inc., "An Introduction to Aerosol Propellants", Retrieved May 2015.

* cited by examiner

COMPOSITION AND KITS FOR INHIBITION OF PATHOGENIC MICROBIAL INFECTION AND METHODS OF USING THE SAME

CROSS-REFERENCE TO RELATED APPLICATIONS

The present application is a divisional application of U.S. patent application Ser. No. 14/504,079, filed Oct. 1, 2014, and claims the benefit thereof, the entirety of which is incorporated herein by reference for all purposes.

FIELD OF INVENTION

This invention relates generally to the treating, reducing, ameliorating, preventing or inhibiting pathogenic microorganism ingress to a human or animal host, reducing the potential for infection, particularly by necrotizing fasciitis originating microorganisms, through use of an antimicrobial polymer coating barrier that facilitates sustained release of biocidal agents active against such microorganisms. Such formulations are effective for inhibiting microbial ingress pertaining to soft tissue and skin tears, abrasions, punctures and surgical wounds, and can be used as in water environments and as a sunscreen and insect repellent.

BACKGROUND OF THE INVENTION

Opportunistic pathogens are usually described as organisms that can become pathogenic following a change to their host, particularly by an immunodeficient, compromised immune system, including disease, wounds, skin damage, prior infection, immunosuppression, genetic predisposition, chemotherapy, and ageing. The opportunistic pathogens can originate from environmentally acquired microbes (e.g., *Pseudomonas aeruginosa, Burkholderia cepacia, Vibrio vulnificus*) or from normally commensal symbionts (e.g., *Streptococcus pneumoniae* and *Staphylococcus aureus*. Many other pathogens are opportunists in that although they can cause disease in healthy humans, they are also zoonotic and can exploit other hosts (e.g., *Bacillus anthracis, Cryptosporidium parvum, Giardia duodenalis, Mycobacterium* spp., *Salmonella, Campylobacter* spp., West Nile virus, and rabies virus).

Pathogenic bacteria can cause disease because they possess certain structural, biochemical, or genetic characteristics that render them pathogenic or virulent. The pathogenicity of microorganisms is expressed by means of their virulence, a term which refers to the degree of pathogenicity of the microbe. Hence, the determinants of virulence of a pathogen are any of its genetic or biochemical or structural features that enable it to produce disease in a host. Some pathogens may rely on a single determinant of virulence, such as toxin production, to cause damage to their host, e.g., bacteria such as *Clostridium tetani* and *Corynebacterium diphtheria*. Other pathogens, such as *Staphylococcus aureus, Streptococcus pyogenes,* and *Pseudomonas aeruginosa*, have a large array of virulence determinants and can produce a wider range of diseases that affect different tissues in a host.

*Candida albicans* is a species of fungus that typically resides in the gastrointestinal tracts. It is also the most common human fungal pathogen, causing a variety of skin and soft tissue infections in healthy people and more virulent invasive and disseminated diseases in patients with compromised immune systems. Although it is normally a harmless commensal organism, it can be an opportunistic pathogen for immunocompromised people and can cause painful mucosal infections in addition to severe, life-threatening bloodstream infections and subsequent infections to internal organs.

A healthy human or animal can normally defend itself against pathogens at different stages in the infectious disease process. The host defenses may prevent infection entirely. However, the defenses that are necessary may not be effective when infectious disease is well established. Chemotherapy is a major defense against bacterial infection, particularly with antibiotics, but bacterial resistance to antibiotics has become part of a pathogen's determinants of virulence.

Recently, necrotizing fasciitis has become a significant pathogenic infection. In general, necrotizing fasciitis refers to a rapidly spreading infection, usually located in fascial planes of connective tissues that results in tissue necrosis. Fascial planes are bands of connective tissue that surround muscles, nerves, and blood vessels, which bind structures together as well as allow body structures to slide over each other effectively. Once necrotizing fasciitis occurs, the infection rapidly destroys muscle, skin, and fat tissue. The disease can occur in almost any area of the body. Although many cases have been caused by Group A beta-hemolytic streptococci (*Streptococcus pyogenes*), many different bacterial genera and species, either alone or together (polymicrobial), can cause this disease. Occasionally, fungal species cause necrotizing fasciitis.

Variations of necrotizing fasciitis are often designated into three general groups or types. Type 1 is either caused by more than two bacterial genera (polymicrobial) or by the less frequently found single bacterial genus such as *Vibrio* or fungal genera such as *Candida*. Type 2 is caused by *Streptococcus* bacteria, and type 3 is caused by *Clostridium* bacteria. Bacteria cause most cases of necrotizing fasciitis; only rarely do other organisms such as fungi cause this disease. Type 1 often occurs after trauma or surgery and may form little or undetectable amounts of gas. Type 2 usually occurs after more simple skin trauma (cuts, abrasions, and insect bites) and infects more superficial facial planes with almost no gas formation. Type 3 usually occurs after trauma or after wounds become contaminated with dirt that contains *Clostridium* bacteria, which produce gas in tissues (gangrene) and necrotic eschars.

Group A *Streptococcus* and *Staphylococcus*, either alone or with other bacteria, cause many cases of necrotizing fasciitis. Bacterial genera such as *Bacteroides, Peptostreptococcus,* and *Clostridium* are often cultured from the infected area, as well as other bacterial types such as *Escherichia coli, Klebsiella, Pseudomonas. Vibrio vulnificus*, also causes the disease when a person, particularly with liver problems (such as, alcoholics or immunosuppressed patients), eats contaminated seafood, or a wound becomes contaminated with seawater containing the microorganism. For a human host, the main pathogens acquired topically from fish through spine puncture or open wounds are *Aeromonas hydrophila, Edwardsiella tarda, Erysipelothrix rhusiopathiae, Mycobacterium marinum, Streptococcus iniae, Vibrio vulnificus* and *Vibrio damsela*. In general, bacteria that cause necrotizing fasciitis produce toxins that inhibit the immune response, damage or kill tissue, produce tissue hypoxia, specifically dissolve connective tissue, or do all of the above. In polymicrobic infections, one bacterial genus may produce one toxic factor (for example, *Escherichia coli* causing tissue hypoxia), while different types of co-infecting bacteria may produce other toxins that disintegrate damaged tissue cells or connective tissue. A break in the skin is usually needed for these flesh-eating bacteria to cause disease. The initial infection can be from almost any cause (for example, cuts on the skin, abrasions, puncture wounds, surgical incisions, or insect bites). Instead of healing, the infected site can show erythema and swelling. The site may become sensitive to pain, even past the area of erythema and may tingle, with patients often experiencing fever and chills. Early symptoms resemble those of cellulitis, but progressive skin changes such as skin ulceration, thin-walled fluid-filled blister (bullae) formation, necrotic scars (black scabs), gas formation in the tissues, and fluid draining from the site can occur rapidly as the infection progresses. Some patients can become septic, wherein the infection has spread to the bloodstream and throughout the body before the skin changes are recognized, especially when flesh-eating disease begins in deep facial planes. A surgeon is needed immediately if necrotizing fasciitis is suspected or preliminarily diagnosed.

Certain pathogenic microorganisms are believed known for causing necrotizing fasciitis, which is often represented by the media as "flesh eating infection," "flesh eating bacteria," or "flesh eating disease." Many types of bacteria can cause necrotizing fasciitis, including Group A *streptococcus* (*Streptococcus pyogenes*), *Staphylococcus aureus*, *Vibrio vulnificus*, *Clostridium perfringens*, *Bacteroides fragilis*, *Aeromonas hydrophila*, *Klebsiella* spp., *Clostridium perfringens*, *Escherichia coli*, *Staphylococcus aureus*, *Peptostreptococcus* spp., *Prevotella* spp., *Porphyromonas* spp., *Haemophilus influenzae* type b, *Vibrio damsela* (*Photobacterium damsela*), and *Vibrio parahaemolyticus*.

Although necrotizing fasciitis often results from beta-hemolytic streptococci infection associated with a minor injury, it is now recognized as also being due to *Vibrio vulnificus*, particularly in fishermen and those in contact with warm water. *Vibrio vulnificus* may cause rapidly progressive necrotizing fasciitis, septicemia and death, while several other species of *Vibrio* have also been incriminated. Treatment for *Vibrio vulnificus* infections often includes antibiotics and/or aggressive wound care. Recommended antibiotic therapy for *Vibrio vulnificus* infection may include doxycycline intravenously or orally, ceftazidime intravenously, or other third-generation cephalosporin, with severe wound infections potentially requiring surgical debridement, fasciotomy, or limb amputation.

In International Publication Number WO 2006/131401, a method of controlled release of a drug through skin is reported, which method comprises topically administering a composition that comprises at least one solubilized drug, a film-forming silicone, and at least one volatile solvent, wherein the drug may be vitamin D or a vitamin D analog or a corticosteroid, the film-forming silicone is a polyorganosiloxane elastomer, which is chemically crosslinked and which exhibits viscoelastic properties and is the form of a viscous and translucent gel, and where the preferred volatile solvents include alkanols, alkylglycols, alkylketones and/or alkyl esters, wherein the alkyl moieties contain from 1 to 6 carbon atoms, preferably from 1 to 4 carbon atoms, such as ethanol, isopropanol, n-butanol, ethyl acetate, acetone, and mixtures thereof. Volatile silicone solvents having 2 to 10 silicone atoms may also be used. The preferred volatile solvent is ethanol. The composition is preferably in the form of a cream, gel, ointment, or pomade.

In U.S. Pat. No. 4,374,126, a method and composition for a film-forming antimicrobial material for animal skin is reported wherein said film is resistant to body fluids and provides long term protection against microorganisms. The composition comprises an alcohol soluble carboxylated polyacrylate that is soluble in alkaline water, as well as, many organic solvents, to which is added an antimicrobial agent, a topical adhesion promoter, and a difunctional amide that crosslinks the polymer as the solvent evaporates. Within the composition there may be incorporated antimicrobial agents such as antibacterials, antiseptics, antifungals, anti-infectives, and antibiotics. Examples of such antimicrobial agents are bacitracin, polymyxin B sulfate-bacitracin-neomycin, nystatin, chlorhexidine, iodine, sulfisoxazole, iodoform, polymyxin B, sulfate, griseofulvin and neomycin sulfate. The topical film once formed does not resolubilize in alcohol or other common sterilants because of its cross-linked behavior. The topical film is reported to adhere to tissue and is resistant to physical removal and to abrasion.

In U.S. Pat. No. 5,417,968, a moisture-activated, antimicrobial barrier composition is provided that can be applied to human skin, especially the hands prior to donning disposable latex gloves. In a preferred embodiment, this composition contains one or more quaternary ammonium compounds and nonoxynol-9 in a functional complex as the pathogenic growth inhibitor. The composition provides a waterproof protective barrier lasting 6 or more hours, which remains inert until it comes into contact with bodily secretions, sweat, water, or other liquid, wherein a hydrophilic polymeric component of the composition breaks down and precipitates upon contact with moisture, thus activating the composition. The barrier composition, once activated, continues to afford protection for up to 4 hours.

In U.S. Patent Application 2003/0147925, a non-eluting topical antimicrobial composition containing an antimicrobial complex that provides sustained antimicrobial disinfecting action upon contact with microorganisms for prolonged periods is presented, without the necessity for reapplication. The topical dermal antiseptic compositions contain a self-preserving antimicrobial biguanide polymer, poly(hexamethylene biguanide) (PHMB), that can bind non-leachably to a surface, exhibits sanitizing properties when applied on skin, forms microbial barrier films in situ that are moisture and sweat resistant, and provides "persistence" or extended duration residual antimicrobial efficacy in water contacting environments, and deodorizing action that is moisture and sweat resistant.

U.S. Patent Application 2007/0048344 discloses a chemical treatment for controlling the spread of pathogens and infection diseases that may be applied to material substrates and protective articles, wherein the antimicrobial composition involves a synergistic mixture of active agents, including a primary antimicrobial agent, such as poly(hexamethylene biguanide), a secondary antimicrobial agent, and optionally an anti-static agent or a fluoropolymer. The substrate may encompass both woven and nonwoven fabrics made from either natural or synthetic fibers or combination blends of the two, elastic and non-elastic, porous and non-porous membranes or films, and laminates or combinations thereof. Other substrates may include rubber, plastic, or other synthetic polymer materials, or metal, steel, glass or ceramic materials. The composition is stable on the substrate surfaces to which it may be applied, so that it does not tend to leach out from the applied surface.

In U.S. Pat. No. 6,582,683, a dermal barrier composition for topical application is provided by the invention that is particularly suitable for health care, food service and other environments where harsh or toxic materials may be encountered, wherein the dermal barrier composition contains a hydrophilic polymer emulsion and a hydrophobic polymer emulsion. The dermal barrier composition is itself an emulsion, and can optionally contain a biocidal agent for antimicrobial and antiviral efficacy. The dermal barrier composition can also contain other active agents such as sunscreens, insect repellents and fungicides. The dermal barrier composition can be applied topically to skin, where it forms a protective or barrier layer against a number of pathogenic and chemical irritants. The composition is temperature, moisture and substrate activated. This means that when the composition encounters a suitable substratum such as skin at a temperature above ambient and under dehydrating conditions, the composition undergoes conformational changes. As a result of the conformational changes, helical fibers within the composition align with each other, creating "sticky ends" which result in a barrier matrix of high molecular weight. These fibers become nearly irreversibly bound to the substrate by very strong ionic, hydrophilic and hydrophobic forces.

In U.S. Pat. No. 8,343,523, a disinfectant composition is provided comprising an alcohol-soluble, water-insoluble, antimicrobial polymer suitable for disinfecting and for providing a prolonged antimicrobial property to a variety of surfaces, including skin. The disinfectant composition comprises an antimicrobial polymer in an alcohol- or glycol-containing solvent, wherein the antimicrobial polymer is readily soluble in the alcohol or glycol, but insoluble in water, and wherein the solvent serves as a carrier for applying said antimicrobial polymer to a surface, whereby said surface acquires a coating of the antimicrobial polymer. The antimicrobial polymer is selected so that its antimicrobial activity occurs by virtue of a contact-killing mechanism, which does not require leaching, elution, or releasing into contacting fluids at levels that would result in fluid disinfection.

In U.S. Patent Application 2014/0127320, a composition and method adapted for delivery of hydrophilic, biologically-active agents to and through the protective outer layer of a biological surface are disclosed. The composition can include a reverse microemulsion formed from at least one hydrophilic, biologically-active agent solubilized by a hydrophobic reverse emulsion surfactant in a non-stinging, volatile, hydrophobic solvent. The hydrophobic reverse emulsion surfactant that provides a water-in-oil microemulsion is based primarily on sodium bis(2-ethylhexyl)sulfosuccinate. In some embodiments, the compositions can be active antimicrobial agents against at least one microbe selected from the group consisting of Gram-negative bacteria, Gram-positive bacteria, and fungi. As a substrate carrier for the sustained release of the biologically-active agents incorporated within the reverse emulsion surfactant, with or without other additives, polymers utilized in non-stinging, liquid adhesive bandages are preferred. In some embodiments, liquid adhesive bandages are prepared from siloxy-containing hydrophobic polymers admixed with volatile liquid polydimethylsiloxanes and volatile liquid alkanes that provide non-stinging, non-irritating liquid bandage coating materials after solvent evaporation.

U.S. Pat. No. 7,670,997 reports an aqueous ophthalmic composition comprising a branched, glycerol monoalkyl compound, selected from a branched, glycerol monoalkyl ether (such as 3-[(2-ethylhexyl)oxy]-1,2-propanediol, also called octoxyglycerin), a branched, glycerol monoalkyl amine, or a branched, glycerol monoalkyl sulfide, or any mixture thereof, and a fatty acid monoester, such as decanoyl glycerol, wherein the aliphatic fatty acid portion is a straight chain, saturated or unsaturated hydrocarbon with eight to ten carbons, or a branched chain, saturated or unsaturated hydrocarbon with eight to ten carbons. The composition can contain an antimicrobial, such as poly (hexamethylene biguanide), at a concentration of 1 ppm to 100 ppm. A method of inhibiting the formation of foam in an aqueous ophthalmic composition that includes a surfactant as well as to a method of enhancing the biocidal efficacy of an aqueous ophthalmic composition containing a fatty acid monoester is also disclosed.

In U.S. Patent Application 2013/0150451, an antimicrobial composition with synergistic biocidal activity is described that comprises at least one antimicrobial polymeric biguanide and at least one antimicrobial vicinal diol, where the vicinal diol comprises at least one monoalkyl glycol, monoalkyl glycerol, or monoacyl glycerol, to diminish or eliminate microbial biofilm communities. Such synergistic interaction is reported to be effective in wound treatment involving biofilms, particularly for chronic wounds, burns and battlefield-induced wounds, as well as for disinfecting non-biological surfaces. The antimicrobial composition is preferably prepared as viscous aqueous solutions or as hydrated gels. In addition, the antimicrobial composition may be dried on to a substrate, such as to a catheter, foam, or fiber wound dressing, or coated as a viscous aqueous solution or hydrated gel upon such devices, to provide controlled release antimicrobial activity.

In U.S. Patent Application Number 2013/0261534, an apparatus and method for wound, cavity, and bone treatment is provided. The apparatus contains a reservoir or generator for a treatment solution, a mechanism for delivering the treatment solution to a wound site, a mechanism for applying the solution to a wound, tissue, bone or surgical cavity for treatment. and optionally for applying negative pressure to, for example, a wound. The apparatus may apply the solution (e.g., a solution containing hypohalous acid) with, for example, an occlusive wound dressing, pulsative lavage device, hydrotherapy, hydrosurgical device, and/or ultrasound. Necrotizing fasciitis is a life-threatening condition and it is characterized by bacterial infection of the skin, including the subcutaneous tissue and superficial fascia. As disclosed, infusion of hypochlorous acid (HOCl) solution to patients with necrotizing fasciitis advances the wound healing process. In addition, since hydrosurgery can be painful for the patient, a hypohalous acid reduces the amount of pain associated with the procedure, thereby making the procedure more tolerable. Further, use of hypohalous acid reduces cross contamination/microbial contamination and aerosolization of bacteria during the hydrosurgery procedure, providing a safer wound care environment for all patients.

U.S. Pat. No. 5,916,541 reports an improved sunscreen protection and insect repellent composition having an SPF factor of about 2 to about 50 and having an unusually long efficacy period when used in rainy conditions or prolonged periods of high humidity, such as in tropical or sub-tropical rain forests, or the like, and after the wearer has been underwater. The composition includes a sunscreen agent, an insect repellent, an emulsifying agent, and a film former, all in an aqueous solvent. The composition forms a stable emulsion lotion that is easy to store. When applied, a thin film is formed on the skin that is non-greasy to the touch and resists water, yet it is readily removed by scrubbing with soap and water.

U.S. Pat. No. 6,180,127 discloses slow release formulations for use for application of volatile insect repellents. A copolymer of polyvinylpyrrolidone and an alkyl group of 4 to 30 carbons provides the slow release properties. The formulations are characterized by high residual action, low skin penetration, and high resistance to removal by water, said polymer formulated in a suitable formulation with a volatile insect repellent, preferably N,N-diethyltoluamide (DEET). Preferred alkylated polyvinylpyrrolidone embodiments of this invention are the hexadecene copolymer of polyvinylpyrrolidone (PVP), the eicosene copolymer of PVP and the 1-triacontene copolymer of PVP. Preservatives that are known in the art to be useful therein include: Quaternium-15, methyl paraben, propyl paraben, dihydroxydimethyl hydantoin, benzyl alcohol, methyl chloroisothiazolinone and methyl isothiazolinone, butyl paraben, imidazolidinyl urea, diazolidinyl urea, disodiumethylenediamine tetraacetic acid and tetrasodiumethylenediamine tetraacetic acid and mixtures thereof. The quantities of such agents used may vary depending on the combination and the levels required to prevent microbial growth.

U.S. Patent Application 2013/0251773 reports the controlled release of insect repellents through a polymeric matrix, and more specifically, polymer matrices comprising ethylene copolymers, ethyl celluloses, and/or thermoplastic polyurethanes, which may optionally include at least one insect repellent synergist, at least one additive, at least one additional polymer, and any combination thereof. One embodiment of that disclosure provides for a method that includes mixing an insect repellent in a polymer melt. Another embodiment provides for a layered article that includes an adhesive layer; and an insect repellent layer comprising a controlled release insect repellent material. A further embodiment provides for a molded article that includes a controlled release insect repellent material. Yet another embodiment of that disclosure provides for a fabric that includes a controlled release insect repellent material in fiber form. Suitable physical forms of the invention include articles, fibers, sheets, pellets, particles, molded articles, such as a bottle, a bucket, or candle-shapes, and the like.

In U.S. Patent Application 2012/0115812, skin coating compositions and methods of application thereof and, in particular, coatings (i.e., films) containing an active agent are reported. In some embodiments, the coating composition includes a polymer, e.g., hydrophilic polymers, such as certain acrylics, amines, ethers, styrenes, vinyl acids, and vinyl alcohols. In some embodiments, the coating may be applied to a skin surface and may be essentially colorless and transparent. In some aspects, the coating comprises a polymer and an active agent, and the polymer may be configured for sustained release of the active agent. In some aspects, the coating forms a barrier essentially impermeable to microorganisms yet permeable to water vapor. In some embodiments, the polymer and/or active agent are dissolved and/or suspended in an alcohol solvent. In some embodiments, the alcohol may function as an antiseptic on skin. The coating compositions and methods may be used for drug delivery to a tissue surface, protection from damaging sources, antimicrobial and/or antiviral applications, sunscreen, pest repellent, an increase or reduction of friction between two surfaces, and/or ease of cleaning. In some aspects, a coating composition may be used to deliver an agent through the skin. In some embodiments, an agent released from the coating may be absorbed through the skin. In some embodiments, the agent may be selected from organic compounds, inorganic compounds, proteins, nucleic acids, and/or carbohydrates. In some embodiments, the agent may be a pharmaceutical agent. In certain aspects, the pharmaceutical agent may be used to treat the skin. For example, an agent may be an antimicrobial agent (i.e., antiviral, antibacterial, antifungal, etc.), an anti-acne agent, a corticosteroid, nicotine, hormones, or anti-inflammatory compounds. The coating composition may have antimicrobial and/or antiviral properties, which may be used in settings such as households, hospitals, clinician offices, food services, schools and daycares, nursing homes, gyms and health clubs, janitorial services, and/or pools or spas. A coating composition may also be used as a skin protectant spray, a first aid for temporary protection of minor cuts, scrapes, burns, etc., and/or a hand sanitizer with residual germ-killing strength. In some aspects, the coating composition is soluble in an organic solvent. Suitable organic solvents are either volatile or non-volatile, including alcohols (i.e., methanol, ethanol, to isopropanol, butanol, pentanol, hexanol, isomers thereof, etc.), dimethylsulfoxide, N,N-dimethylformamide, N-methylpyrrolidone, hexamethyldisiloxane, gamma-butyrolactone, glycol ethers, terpene solvents, ester solvents (i.e., ethyl acetate), acetone, mixtures thereof, and the like. In some embodiments, an essentially immediate antiseptic effect is provided by an alcohol and/or a quaternary amine (i.e., benzalkonium chloride). In some embodiments, the efficacy of the essentially immediate antiseptic effect may be greater than 99.9% of microorganisms killed within 5 seconds, within 15 seconds, within 30 seconds, or within 1 minute.

SUMMARY

This invention relates generally to the inhibition, treatment, amelioration, and reduction of pathogenic microorganism ingress to a human or animal host, reducing the potential for infection, particularly microorganisms that cause necrotizing fasciitis through use of an antimicrobial polymer coating barrier that facilitates sustained release of biocidal agents active against such opportunistic microorganisms. Such formulations are effective for inhibiting microbial ingress pertaining to soft tissue and skin tears, abrasions, punctures and surgical wounds, and can be used in water environments and as a skin protectant sunscreen and insect repellent.

The present invention provides an antimicrobial polymer coating composition that is capable of sustained release of biocidal agents against the opportunistic pathogens of *Candida albicans, Vibrio vulnificus, Pseudomonas aeruginosa, Staphylococcus aureus, Streptococcus pyogenes,* and *Escherichia coli* for at least 24 hours. Similar sustained biocidal behavior of the antimicrobial composition is noted with the addition of sunscreen agents, which are useful in protecting skin against UVA and UVB radiation with an SPF of at least 10, at least 20, at least 30, at least 40, or at least 50. Similar antimicrobial compositions are useful as insect repellents.

In some embodiments, it has unexpectedly been discovered that a polymeric biguanide, particularly poly(hexamethylene biguanide) (PHMB), in conjunction with at least one additional antimicrobial agent in a water-insoluble polymer coating demonstrates significant sustained inhibition and reduction of opportunistic pathogenic microorganisms, particularly from bacteria, including *Vibrio vulnificus, Streptococcus pyogenes*, methicillin-resistant *Staphylococcus aureus, Pseudomonas aeruginosa*, and *Escherichia coli*, and from yeast, including *Candida albicans*. In some embodiments the combination of PHMB with the hydrophobic monoacyl glycerol, glycerol monolaurate, gave unexpected results in the polymer coating's ability to reduce opportunistic pathogenic microorganisms. Surprisingly, although PHMB is active against many types of microorganisms, glycerol monolaurate, an antimicrobial agent that has potent activity against deodorant Gram-positive bacteria, the combination of both PHMB and glycerol monolaurate unexpectedly exhibited greatly enhanced biocidal activity against necrotizing pathogens, Gram-negative *Vibrio vulnificus* and Gram-positive *Streptococcus pyogenes*, an activity that did not occur when glycerol monolaurate was not present. Similar, unexpected activity was exhibited by mixtures of PHMB with alexidine hydrochloride, chlorhexidine (e.g., chlorhexidine digluconate, chlorhexidine diacetate), benzethonium chloride, and mixtures thereof.

The phenomenon of topically inhibiting such opportunistic pathogens from infecting a host in a sustained release manner with a biguanide polymer and at least one additional antimicrobial agent in a water-insoluble polymer coating has not been previously reported.

The active polymer coating described herein is applied in liquid form and air dried at room or body temperature on a skin, tissue or mucous membrane surface to form an adherent, water-insoluble, conformable, non-biodegradable, protective film containing the active antimicrobial agents. The liquid coating solution can be applied by spraying, wiping, dipping, painting, casting, brushing, and by aerosol propellants, or by other conventional coating methods, to coat a biological surface.

In some embodiments, the polymer component of the liquid adhesive material comprises film-forming polymers from commercial sources, preferably those used in personal care, cosmetic, and pharmaceutical applications. In some embodiments, a synthetic film-forming polymer can be obtained by a hydrophobic, hydrophilic, or amphiphilic vinyl-type monomer that is polymerizable, preferably by free radical initiation, and is either neutral, cationic, or ampholytic in charge, with one or more free radically polymerizable comonomers that are either hydrophobic, hydrophilic, or amphiphilic, resulting in co-polymers to multi-polymers that are either neutral, cationic, or ampholytic in charge. Preferably, the resulting polymer coating (after solvent evaporation) is water-insoluble and adheres to a biological surface. The composition of the polymer coating modulates properties such as solubility in volatile solvents, adhesion to a biological surface, air surface tack, tear strength, clarity, extensibility, flexibility, puncture strength, water-vapor transmission, oxygen permeability, plasticization, refractive index, gloss, dirt (debris) pick-up, re-coatability, the glass transition temperature, hydrophilicity, hydrophobicity, ability to hydrogen bond (to active biological agents and skin/tissue), ability to provide sustained release of active biological agents, allergic response, and the like.

In some embodiments, a free radically polymerizable siloxanyl-containing monomer is a component of the polymer coating because of its inherent water-vapor and oxygen permeability. Such monomers, are cited in U.S. Pat. Nos. 5,103,812, 7,622,512, 7,795,326 and 8,263,720, as well as, Applicant's co-pending U.S. patent application Ser. No. 14/046,591, the entireties of which are incorporated herein by reference.

The coating polymers can be solubilized in either non-polar or polar volatile solvents, or combinations thereof. Examples of non-polar solvents that can be used in the volatile solvent include, but are not limited to, volatile linear and cyclic siloxanes, volatile alkanes, volatile cycloalkanes, volatile chlorocarbons, volatile chlorofluorocarbons, volatile fluorocarbons, and combinations thereof. Examples of polar solvents that can be used in the volatile solvent include, but are not limited to, volatile alcohols, volatile esters, volatile ketones, volatile ethers, and, if needed, a lesser quantity of solubilized water, and combinations thereof. In some embodiments, the antimicrobial compositions can by aerosolized by a propellant.

In some embodiments, antimicrobial compositions that absorb ultraviolet radiation are described. Such antimicrobial compositions can be applied to skin as a polymer coating that provides protection against the effects of such radiation. A preference is given to sunscreen agents protective against UVA and UVB radiation. Intense sun exposure can result in sunburn, which increases the risk of skin damage and certain diseases, including infection, wherein ruptured blisters increase susceptibility to opportunistic microbial infection, in addition to photoaging of skin, and skin cancer.

In some embodiments, our invention also relates to antimicrobial compositions that function as insect repellents are described. It is well recognized that outdoor activities are often hampered by biting and stinging insects, such as mosquitoes, flies, bees, hornets, wasps, yellow jackets, noseeums (biting midges), gnats, sand flies, scorpions, chiggers, punkies, ticks, head lice, fire ants, fleas, spiders, scabbies, and other insects. Many biting/stinging insects such as fleas, mosquitoes, and flies, are vectors for serious diseases, such as malaria, Rocky Mountain spotted fever, Lyme disease, leishmaniasis, dengue fever, and West Nile fever. Malaria is a mosquito-borne infectious disease caused by parasitic protozoans of the genus *Plasmodium*. Malaria is often transmitted by a bite from an infected female *Anopheles* mosquito, which introduces the organisms from its saliva into a human or animal circulatory system. No effective vaccine exists for malaria, and disease transmission can be reduced by preventing mosquito bites by using mosquito nets and insect repellents, or by spraying insecticides and by draining standing water. Rocky Mountain spotted fever is caused by *Rickettsia rickettsii*, a species of bacterium that is spread to humans by *Dermacentor* ticks. Rocky Mountain spotted fever can be a severe or even fatal illness if not treated in the first few days of symptoms; it responds well to prompt treatment with antibiotics. Lyme disease is an infectious disease caused by at least three species of bacteria belonging to the genus *Borrelia*. Leishmaniasis is a disease caused by protozoan parasites of the genus *Leishmania* and spread by the bite of certain types of sandflies. Leishmaniasis can be partly prevented by sleeping under nets treated with insecticide, as well as by spraying insecticide to kill sandflies and treating people with the disease early to prevent further spread. Dengue fever is a mosquito-borne tropical disease caused by the dengue virus. For dengue fever, there is no commercially available vaccine and prevention is based upon limiting access of mosquitoes to the habitat and eliminating exposure to bites. West Nile infection is caused by a virus transmitted by mosquitoes. Reducing the risk of being infected with West Nile Virus is by insect repellent and wearing protective clothing, preventing mosquito bites. There are no medications or vaccines to prevent West Nile Virus infection.

It is an object of the invention to inhibit pathogenic microbial infection by opportunistic microorganisms by providing a sustained release of antimicrobial agents active against such pathogens.

It is a further object of the invention to provide a liquid-containing polymer solution in a volatile solvent, where the volatile solvent evaporates readily at room or body temperature to provide a protective polymer coating.

It is a further object of the invention to inhibit pathogenic microbial infection by opportunistic microorganisms by providing a sustained release of antimicrobial agents active against such pathogens from a polymer coating, produced by evaporating a volatile solvent containing the polymer and the antimicrobial agents.

It is a further object of the invention to provide an adhesive, conformable, polymer coating that incorporates the antimicrobial agents.

In another aspect of this invention, polymer coatings are provided that are useful for protecting biological surfaces against exogenous microbial contamination.

It is a further object of the invention to provide an adhesive, conformable, polymer coating that is oxygen permeable.

It is a further object of the invention to provide an adhesive, conformable, polymer coating that is water-vapor permeable.

It is a further object of the invention to provide an adhesive, conformable, polymer coating that is transparent or translucent.

In another aspect, the polymer, when solubilized in a volatile solvent, provides for a fast drying, flexible, water-insoluble, conformable, adherent coating.

It is an object of the invention to provide a polymer-containing coating composition that can protect skin, tissue and mucous membranes from being damaged when applied in liquid form and air dried to form a conformable, adherent, solid protective film.

It is an object of this invention to provide a polymer coating deposited in conjunction with solvent evaporation, wherein the solvent is a volatile liquid that evaporates at room temperature or body temperature.

It is a further object of this invention that the volatile solvent is non-polar, polar, or a combination thereof.

It is a further object of the invention to provide a polymer coating in which antimicrobial agents may be incorporated for sustained release onto targeted areas of skin, tissue, or mucous membranes.

It is a further object of the invention to provide a polymer coating in which antimicrobial agents may be incorporated for sustained release over at least 24 hours.

It is a further object of the invention to provide a polymer coating in which sunscreen agents may be incorporated for protection against UVA and UVB radiation.

It is a further object of the invention to provide a polymer coating in which insect repelling agents may be incorporated for protection against biting and stinging insects.

It is a further object of the invention to provide a polymer coating that includes antimicrobial agents, such as sunscreen agents, and insect repelling agents may be incorporated.

It is a further object of the invention to provide a polymer coating that includes antimicrobial agents, such as poly(hexamethylene biguanide) and its salts.

It is a further object of the invention to provide a polymer coating containing a polymeric biguanide and at least one antibacterial agent, antifungal agent, antiprotozoal agent, antiviral agent, or antibiotic agent.

It is a further object of the invention to provide a polymer coating in which the antimicrobial agents include poly(hexamethylene biguanide) and its salts and hydrophobic monoacyl glycerols.

It is a further object of the invention to provide a polymer coating including a polymeric biguanide and at least one additional antimicrobial agent selected from bis(biguanides) and quaternary ammonium salts.

It is a further object of this invention to provide a polymer coating containing additional antimicrobial agents comprising nitrogen-containing, cationic and amphoteric surface active agents.

It is a further object of the invention to provide a polymer coating that contains essential oils.

It is a further object of this invention to provide a pleasing fragrance to the antimicrobial compositions.

It is a further object of the invention to provide a polymer coating that contains emollients.

It is an object of this invention that the antimicrobial polymer coating compositions described herein treat, reduce, ameliorate, prevent or inhibit pathogenic microorganisms from entering a human or animal host.

It is an object of this invention that the antimicrobial polymer coating compositions described herein can reduce the potential for infection by opportunistic pathogens.

It is an object of this invention that the antimicrobial polymer coating compositions described herein can reduce the potential for necrotizing fasciitis by bacteria of Group A *Streptococcus, Streptococcus pyogenes, Staphylococcus aureus, Vibrio vulnificus, Clostridium perfringens, Bacteroides fragilis, Aeromonas hydrophila, Klebsiella* spp., *Clostridium perfringens, Escherichia coli, Staphylococcus aureus, Peptostreptococcus* spp., *Prevotella* spp., *Porphyromonas* spp., *Haemophilus influenzae* type b, *Photobacterium damsel, Vibrio damsela*, and *Vibrio parahaemolyticus*.

It is an object of this invention that the antimicrobial polymer coating compositions described herein can reduce the potential for necrotizing fasciitis by fungal infection from *Candida albicans*.

It is an object of this invention that the antimicrobial polymer coating compositions described herein can inhibit necrotizing fasciitis.

These and other objectives and advantages of the compositions and method to inhibit pathogenic microbial infection described herein, some of which are specifically described and others that are not, will become apparent from the detailed description and claims that follow.

DETAILED DESCRIPTION

The inhibition and prevention of an opportunistic microorganism from entering a human or animal host has particular relevance to maintaining health. Such inhibition and prevention is critically needed particularly for outdoor activities such as boating, fishing, swimming, wading, working, backpacking, cycling, camping, canoeing, canyoning, caving, cooking, golfing, hiking, horseback riding, hunting, kayaking, lounging, mountaineering, mountain biking, parasailing, photography, racing, rafting, reading, rock climbing, running, sailing, seafood handling, sightseeing, skateboarding, skiing, skimboarding, snowboarding, sledding, sunning, surfing, trekking, walking, water skiing, including all water and other sport, recreational, and work-related activities, wherein such activities can result in insect, animal, fish, leech, mite, tick, spider, flea, and mosquito bites, parasitic infestations, ant stings, bee stings, stonefish stings, jellyfish stings, sunburn, skin abrasions, skin lesions, burns, skin lacerations, skin punctures, skin tears, and the like that facilitate microbial infection.

Of particular concern for the maintenance of health is the potential of acquiring infection by the opportunistic pathogen *Vibrio vulnificus* because this organism prefers warm water, often where recreation occurs, such as fishing, wading, swimming, diving, boating, rafting, surfing, etc. In protecting these individuals against the ingress of pathogenic microorganisms caused by an open wound or by disruption of a skin or tissue surface, a water-insoluble polymer coating containing a composition of an antimicrobial polymeric biguanide with at least one additional antimicrobial agent surprisingly enhances biocidal activity against microorganisms associated with causing necrotizing fasciitis. Additionally, since such environments often occur in sunny conditions and in outdoor environments, sunscreen lotion application and insect repellent use is common, and this invention additionally includes antimicrobial compositions for protection against UVA and UVB radiation, as well as for protection against insect bites.

In some embodiments, an antimicrobial, water-insoluble, polymer coating composition is disclosed. The antimicrobial, water-insoluble, polymer coating composition can include at least one polymeric biguanide in an amount from at least 0.10 wt % to 10.00 wt %, at least one additional antimicrobial agent in an amount of at least 0.20 wt % to 10.00 wt %, and a polymer coating comprising up to 99.7 wt % of the composition, wherein the polymer coating composition provides sustained biocidal activity against opportunistic pathogens for at least 24 hours.

The compositions described herein include both liquid coating compositions and the polymer coatings cast from those coatings. Thus, the ingredients of the liquid coating compositions and the polymer coatings described herein can be identical, with the exception of the volatile components (e.g., the volatile solvent). Furthermore, amounts of the ingredients will differ primarily by the presence or absence of the volatile components (e.g., primarily the volatile solvent).

In some embodiments, the polymer coating composition is a dried film. In some embodiments, the polymeric biguanide comprises poly(hexamethylene biguanide) and its salts.

In some embodiments, the additional antimicrobial agent is selected from the group consisting of an antibacterial agent, an antifungal agent, an antiprotozoal agent, an antiviral agent, an antibiotic. In some embodiments the additional antimicrobial agent is selected from the group consisting of monoacyl glycerols, monoalkyl glycols, bis (biguanides), glycerol monolaurate, chlorhexidine, chlorhexidine digluconate, chlorhexidine diacetate, alexidine, alexidine dihydrochloride, silver salts, benzalkonium chloride, benzethonium chloride, gentamicin sulfate, iodine, povidone-iodine, starch-iodine, neomycin sulfate, polymyxin B, bacitracin, tetracyclines, clindamycin, gentamicin, nitrofurazone, mafenide acetate, silver sulfadiazine, terbinafine hydrochloride, miconazole nitrate, ketoconazole, clotrimazole, itraconazole, metronidazole, antimicrobial peptides, polyquaternium-1, polyquaternium-6, polyquaternium-10, cationic guar, water-soluble derivatives of chitosan, salts thereof, and combinations thereof.

In some embodiments, the polymeric biguanide is poly (hexamethylene biguanide) hydrochloride and the at least one additional antimicrobial agent is selected from the group consisting of glycerol monolaurate, alexidine hydrochloride, chlorhexidine diacetate, benzethonium chloride, and mixtures thereof.

In some embodiments, the polymer coating composition also includes at least one additional additive selected from the group consisting of surfactants, sunscreen agents, insect repelling agents, emollients, active pharmaceutical agents, antibiotics, essential oils, polymer film flexibilizers, plasticizers, compatabilizers, and skin care additives.

In some embodiments, when applied to a surface, the polymer coating composition provides a log reduction of at least 2 log orders in 48 hours against at least one pathogenic microorganisms selected from *Vibrio vulnificus, Pseudomonas aeruginosa, Staphylococcus aureus, Streptococcus pyogenes*, and *Candida albicans*. In some embodiments the log reduction is at least 3 log orders (99.9% kill rate), at least 4 orders (99.99% kill rate), or at least 5 log orders (99.999% kill rate) in 48 hours.

In some embodiments, a film-forming polymer that is soluble in a polar solvent such as ethanol or isopropanol, and insoluble in water may incorporate antimicrobial agents and other additives. Such film-forming polymers are water-resistant and include poly(vinyl acetate-co-butyl maleate-co-isobornyl acrylate), available from Sigma Aldrich; acrylates/octylacrylamide (N-tert-octylacrylamide) copolymer, available from AkzoNobel as DERMACRYL® 2.0; octylacrylamide/acrylates/butylaminoethyl methacrylate copolymer, available from MakingCosmetics Inc. as Acrylate Copolymer or from AkzoNoble as AMPHOMER®; methacrylic acid, methyl methacrylate, butyl acrylate, cetyleicosinyl methacrylate copolymer, available as SOLTEX™ OPT from Dow Chemical; poly(N-vinylpyrrolidone/1-triacontene) (Tricontanyl PVP), available as Ganex® WP 660 from Ashland Inc.; and VP/Eicosene copolymer (N-vinylpyrrolidone and 1-eicosene), available from Ashland Inc. as Ganex® V-220F, styrene/acrylates copolymer (copolymer of butyl acrylate and styrene), available from AkzoNobel as DERMACRYL® E, and combinations thereof. The acrylate/octylacrylamide copolymer is believed to be a copolymer of acrylic and methacrylic acid, their esters, and octylacrylamide, such as 2-methylpropyl methacrylate, acrylic acid, and N-tert-octylacrylamide (N-(1,1,3,3-tetramethylbutyl)acrylamide), whereas the octylacrylamide/acrylates/butylaminoethyl methacrylate copolymer may also incorporate 2-(tert-butylamino)ethyl methacrylate.

Other film-forming polymers can be used in the composition, wherein such polymers can be selected from acrylate copolymers; 2-ethylhexyl acrylate/butyl acrylate/VA (Vinyl Acetate) copolymer; methoxy amodimethicone/silsesquioxane copolymer; AMP (AminoMethylPropanol salt)/acrylate copolymers; butylated PVP (PolyVinylPyrrolidone); butyl ester of PVM/MA copolymers (Polymer of Vinyl Methyl ether/Maleic Anhydride); calcium/sodium PVM/MA copolymers; dimethicones; dimethicone copolyol; dimethicone/mercaptopropyl methicone copolymer; dimethicone propylethylenediamine behenate; dimethicolnol ethylcellulose; ethylene/acrylic acid copolymer; ethylene/maleic anhydride copolymer; ethylene/vinyl acetate copolymer; hydrogenated styrene/butadiene copolymer, isobutylene/maleic anhydride copolymer; laurylmethicone copolyol; methyl methacrylate crosspolymers; methylacryloylethyl betaine/acrylates copolymer; nitrocellulose; octadecene/maleic anhydride copolymer, octylacrylamide/acrylate/butylaminoethyl methacrylate copolymer; urethane polymers, polyesters, PVM/MA decadiene crosspolymer; PVM/MA copolymer; PVP/decene copolymer; PVP/dicosene copolymer; PVP/hexadecene copolymer; PVP/MA copolymer; PVP/VA copolymer; steramidopropyl dimethicone; stearylvinyl ether/MA copolymer; styrene/DVB (divinylbenzene) copolymer; styrene/MA copolymer; VA/crotonates copolymer; VA/crotonates/vinyl proprionate copolymer; VA/butyl maleate/isobornyl acrylate copolymer; N-vinylcaprolactam/PVP/dimethylaminoethyl methacrylate copolymer; and combinations thereof.

In some embodiments, the liquid adhesive coating material comprises a hydrophobic, hydrophilic, or amphiphilic vinyl-type polymer obtained from one or more of a vinyl-type monomer that is polymerizable. In some embodiments, the polymer can be prepared by free radical initiation. In some embodiments, the polymer is neutral, ampholytic or cationic in charge. Thus, the vinyl-type polymer can be a hydrophobic, hydrophilic, or amphiphilic homopolymer, copolymer, terpolymer to multi-polymer.

In some embodiments, the addition polymerizable, hydrophobic or hydrophilic vinyl-type monomer is selected from the group consisting of methyl methacrylate, methyl acrylate, ethyl acrylate, ethyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, 2-ethylhexyl acrylate, 2-ethylhexyl methacrylate, isooctyl acrylate, isooctyl methacrylate, n-lauryl acrylate, n-lauryl methacrylate, isodecyl acrylate, isodecyl methacrylate, n-tridecyl acrylate, n-tridecyl methacrylate, cetyl acrylate, cetyl methacrylate, stearyl acrylate, stearyl methacrylate, n-octadecyl acrylate, n-octadecyl methacrylate, eicosyl acrylate, eicosyl methacrylate, cyclohexyl acrylate, tetrahydrofurfuryl acrylate, tetrahydrofurfuryl methacrylate, 2-phenylethyl acrylate, 2-phenylethyl methacrylate, 2-phenoxyethyl acrylate, 2-phenoxyethyl methacrylate, isobornyl acrylate, isobornyl methacrylate, benzyl methacrylate, 2-butoxyethyl acrylate, behenyl methacrylate, 2-hydroxyethyl methacrylate (HEMA), 2-hydroxyethyl acrylate, glyceryl methacrylate, glyceryl acrylate, 4-hydroxybutyl acrylate, poly(ethylene glycol) monoacrylate, poly(ethylene glycol) monomethacrylate, poly(ethylene glycol monomethyl ether) methacrylate, diethylene glycol monoacrylate, diethylene glycol monomethacrylate, triethylene glycol monoacrylate, triethylene glycol monomethacrylate, tetraethylene glycol monoacrylate, tetraethylene glycol monomethacrylate, triethylene glycol methyl ether methacrylate, triphenylmethyl methacrylate, 2-(methacryloyloxy)ethyl acetoacetate, dimethyl itaconate, di-n-butyl itaconate, di-isooctyl itaconate, furfuryl methacrylate, α-methylstyrene, styrene, p-t-butylstyrene, 4-methoxystyrene, 4-aminostyrene, p-hydroxystyrene, vinyl naphthalene, N-vinylcarbazole, vinyl benzoate, butadiene, acrylamide, N-methylacrylamide, N-phenylacrylamide, N-ethylacrylamide, N-[tris(hydroxymethyl)methylacrylamide, N-isopropylacrylamide, N,N-diethylacrylamide, N,N-dimethylacrylamide, N,N-dimethylmethacrylamide, N-diphenylmethylacrylamide, N-(triphenylmethyl) methacrylamide, N-octylacrylamide, N-(1,1,3,3-tetramethylbutyl) acrylamide, N-acryloylamidoethoxyethanol, diacetone acrylamide, N-vinylpyrrolidone, N-vinylcaprolactam, N-vinylformamide, N-vinyl-N-methylformamide, N-vinylacetamide, N-vinylphthalamide, N-(2-methacryloyloxyethyl)ethylene urea, N-(2-methacrylamidoethyl)ethylene urea, 4-acryloylmorpholine, maleimide, N-methylmaleimide, N-(2,3-dihydroxypropyl)maleimide, N-vinylsuccinimide, N-vinyldiacetamide, epsilon-acryloyllysine, N-acryloyluracil, N-acryloylthymine, N-acryloyladenine, N-acryloylguanine, N-acryloylurea, N-acryloylguanidine, N-acrylglucosamine, N-allylpyrrolidone, N-allylacetamide, N,N-dimethylaminoethyl methacrylate, N,N-dimethylaminoethyl acrylate, N,N-diethylaminoethyl methacrylate, N,N-diethylaminoethyl acrylate, N,N-dimethylaminopropylmethacrylamide, N,N-dimethylaminopropylacrylamide, vinylbenzyl-N,N-dimethylamine, methacryloyloxyethylamine, N-vinylimidazole, 4(5)-vinylimidazole, 4-vinylpyridine, 2-vinylpyridine, 2-methyl-5-vinylpyridine, vinyltriazine, salts of cationic monomers, fluorinated monomeric siloxanes, fluorinated itaconate esters, fluorinated methacrylate or acrylate esters, vinyl acetate, (3-acrylamidopropyl)trimethylammonium chloride, [3-(methacryloylamino)propyl]trimethylammonium chloride, (3-methacryloyloxyethyl)trimethylammonium chloride, vinylbenzyltrimethylammonium chloride, and related salts, [3-(methacryloylamino)propyl]dimethyl(3-sulfopropyl)ammonium hydroxide inner salt, [2-(methacryloyloxy)ethyl]dimethyl (3-sulfopropyl)ammonium hydroxide inner salt, and combinations thereof.

In some embodiments, the polymerizable hydroxyalkyl ester containing monomer components are selected from the group consisting of 2-hydroxyethyl acrylate, 2-hydroxyethyl methacrylate (HEMA), 2- and 3-hydroxypropyl acrylate and methacrylate, 2,3-dihydroxypropyl acrylate and methacrylate, 4-hydroxybutyl acrylate and methacrylate, 2-(2-hydroxyethoxy)ethyl methacrylate, 2,3-dihydroxypropyl methacrylate (also known as 1-glycerol methacrylate, glyceryl methacrylate, and glyceryl monomethacrylate), and combinations thereof. Additionally, dihydroxyalkyl esters of unsaturated dicarboxylic acids, such as maleic acid, fumaric acid, and itaconic acid, can also be incorporated. Examples of such esters include, but are not limited to, bis(2-hydroxyethyl)maleate, bis(2-hydroxypropyl)maleate, bis(2-hydroxyethyl itaconate), bis(2-hydroxypropyl)itaconate, and bis(2,3-dihydroxypropyl)itaconate. Hydroxyalkyl esters of ethylenically unsaturated carboxylic acids, including ethacrylic acid, crotonic acid, isocrotonic acid, cinnamic acid, and similar acids of up to about 6 carbon atoms, can be utilized.

In some embodiments, the hydroxyalkyl ester monomers for copolymerization with the siloxysilane monomer are selected from the group consisting of 2-hydroxyethyl methacrylate (HEMA), 2-hydroxyethyl acrylate, 2-hydroxypropyl methacrylate, 3-hydroxypropyl methacrylate, and 2-(2-hydroxyethoxy)ethyl methacrylate, and combinations thereof. In some embodiments, the hydroxyalkyl ester monomer for copolymerization is 2-hydroxyethyl methacrylate.

In some embodiments, the liquid polymer-containing coating material comprises a polymer from an addition polymerizable hydrophobic non-polar alkylsiloxysilane or alkylarylsiloxysilane monomer, with an addition polymerizable, hydrophobic or hydrophilic vinyl-type monomer. In some embodiments, the liquid solvent is alcohol-based, though it may include other solvents. In some embodiments, the hydrophobic vinyl-type monomer component will render the siloxanyl copolymer hydrophobic, potentially increasing adhesion (i.e., duration of attachment) of the polymer coating in aqueous environments, while a polar hydroxyalkyl ester-containing monomer can render the copolymer amphiphilic, the latter of which can contribute to the solubilization of a polar, non-polar, or amphiphilic antimicrobial agent, particularly in a polar volatile solvent, creating an antimicrobial polymer coating barrier that facilitates sustained release of biocidal agents. In some embodiments, the antimicrobial composition forms a water-insoluble coating in the form of a transparent or translucent film when applied to the skin, soft tissue or mucous membrane of a user from a volatile liquid at room temperature or body temperature.

In some embodiments, if a film-forming polymer contains acidic functional groups (such as carboxyl, carboxylate, sulfite, sulfonate, sulfate, phosphonate, or phosphate groups, etc.) that are not neutralized, such groups are capable of ionically interacting with cationic (positively charged) antimicrobial agents, such as PHMB, reducing its ability to function as a sustained release antimicrobial agent. However, the overall composition would be expected to have antimicrobial properties if the film-forming polymer was penetrated. Examples of such film forming polymers include polymers containing acrylate or methacrylate functionality, which have the ability to exist in an anionic (negatively) charged state.

In some embodiments, the addition polymerizable hydrophobic non-polar alkylsiloxysilane and alkylarylsiloxysilane monomer is selected from the group consisting of: 3-methacryloyloxypropyltris(trimethylsiloxy)silane (TRIS), 3-[tris(trimethylsiloxy)silyl]propyl methacrylate (TRIS),
3-methacryloyloxypropylpentamethyldisiloxane,
3-methacryloyloxypropylbis(trimethylsiloxy)methylsilane,
3-methacryloyloxypropyltris(vinyldimethylsiloxy)silane,
3-methacryloyloxymethylbis(trimethylsiloxy)(pentamethyldisiloxanyl)silane,
3-methacryloyloxyethyltris(pentamethyldisiloxanyl)silane,
methacryloyloxymethylbis(trimethylsiloxy)methylsilane,
methacryloyloxymethyltris(trimethylsiloxy)silane,
3-methacryloyloxypropylheptacyclopentyl-T8-silsesquioxane,
3-methacryloyloxypropylheptaisobutyl-T8-silsesquioxane,
3-acryloyloxypropylmethylbis(trimethylsiloxy)silane,
3-acryloyloxypropyltris(trimethylsiloxy)silane,
3-acryloyloxypropylpentamethyldisiloxane,
3-methacryloyloxypropyl-1,1,1-triphenyl-3,3-dimethyldisiloxane,
methacryloyloxymethylphenethyltris(trimethylsiloxy)silane,
di[(trimethylsiloxy)silylpropyl]itaconate,
N-(trimethylsiloxy)silylpropyl maleimide,
p-vinylphenyltris(trimethylsiloxy)silane,
p-vinylbenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentamethyldisiloxane,
vinylphenylbis(trimethylsiloxy)silane,
vinyltris(dimethylsiloxy)silane,
vinyltris(trimethylsiloxy)silane,
allyltris(trimethylsiloxy)silane,
N-tris(trimethylsiloxysilyl)propylmaleimide,
bis(trimethylsiloxy)silylpropyl itaconate,
vinyl-terminated polydimethylsiloxane,
3-(trimethylsilyl)propyl vinyl carbonate,
3-[tris(trimethylsiloxy)silyl]propyl vinyl carbonate,
t-butyldimethylsiloxyethyl vinyl carbonate,
trimethylsilylethyl vinyl carbonate,
trimethylsilylmethyl vinyl carbonate,
polydimethylsiloxane monoacrylate,
polydimethylsiloxane monomethacrylate,
polymethylphenylsiloxane monoacrylate,
polymethylphenylsiloxane monomethacrylate,
monomethacryloxypropyl-terminated polydimethylsiloxanes,
3-acryloyloxypropyltris(polydimethylsiloxanyl)silane,
and combinations thereof.

In some embodiments, the addition polymerizable alkylsiloxysilane and alkylarylsiloxysilane monomer is predominantly hydrophobic, but contains one or more hydrophilic groups capable of hydrogen-bonding to antimicrobial agents, sunscreen agents, and insect repelling agents, as well as other biologically-active substances, wherein such monomers are selected from the group consisting of:
methylbis(trimethylsiloxy)silylpropylglyceryl methacrylate,
tris(trimethylsiloxy)silylpropylglyceryl methacrylate,
3-methacrylamidopropylbis(trimethylsiloxy)methylsilane,
3-methacrylamidopropyltris(trimethylsiloxy)silane,
3-acrylamidopropyltris(trimethylsiloxy)silane,
O-(vinyloxyethyl)-N-(tris[trimethylsiloxy]silylpropyl)urethane,
3-[tris(trimethylsiloxy)silyl]propyl vinyl carbamate,
mono(3-acryloxy-2-hydroxypropoxypropyl)-terminated polydimethylsiloxane,
O-methacryloxyethyl-N-(trimethylsiloxysilylpropyl)carbamate,
O-methacryloxyethoxy-N-[bis(trimethylsiloxy)methylsilyl]propylcarbamate,
N-(3-methacryloxy-2-hydroxypropyl)-3-aminopropyltris(trimethylsiloxy)silane,
(3-methacryloxy-2-hydroxypropoxy)propylbis(trimethylsiloxy)methylsilane,
methacryloyloxy(polyethyleneoxy)propyltris(trimethylsiloxy)silane, and combinations thereof.

In some embodiments, the hydrophobic non-polar alkylsiloxysilane is 3-methacryloyloxypropyltris(trimethylsiloxy)silane (TRIS) (also described as 3-[tris(trimethylsiloxy)silyl]propyl methacrylate).

The volatile liquid solvent can be selected from the group consisting of non-polar solvents, polar solvents, and combinations thereof. In some embodiments, the non-polar solvents can be, but are not limited to, volatile linear and cyclic siloxanes, volatile alkanes, volatile cycloalkanes, volatile chlorocarbons, volatile fluorocarbons, and mixtures thereof. In some embodiments, the polar volatile solvents can be, but are not limited to, volatile alcohols, volatile esters, volatile ketones, volatile ethers, solubilized water, and mixtures thereof. In some embodiments, the volatile liquid volatilizes at room or body temperature (i.e., 72° F. and 98.6° F., respectively). In some embodiments, water is not included in the volatile liquid solvent unless the water is miscible as part of the volatile solvent. In some embodiments, the volatile solvent is anhydrous. As used herein, "volatile liquid solvent," "volatile liquid," and "volatile solvent" are used interchangeably.

As used herein, "non-polar solvent" has its standard meaning in the art and includes solvents with molecules that contain bonds between atoms that have similar electronegativities, such as between carbon and hydrogen in hydrocarbons; bonds between atoms with similar electronegativities lack partial charges and the solvent does not have a permanent electric dipole moment, having no tendency for intramolecular association with polar species.

As used herein, "polar solvent" has its standard meaning in the art and includes solvents with molecules that have a large dipole moment wherein bonds between atoms of the solvent have different electronegativities, such as between oxygen and hydrogen, where there is either a permanent separation of positive and negative charges, or the centers of positive and negative charges do not coincide. Polar solvents have high dielectric constants, such as alcohols and ketones.

Specific examples of volatile nonpolar solvents include, but are not limited to, linear siloxanes, such as hexamethyldisiloxane or octamethyltrisiloxane; cyclic siloxanes, such as hexamethylcyclotrisiloxane or octamethylcyclotetrasiloxane; alkanes, such as, pentane, isopentane, 2-methylpentane, 3-methylpentane, hexane, heptane, octane, isooctane, petroleum distillates, and isomers thereof; cycloalkanes, such as cyclohexane; chlorocarbons, such as chloroform and methylene chloride; and combinations thereof.

Specific examples of polar, volatile solvents include, but are not limited to, alcohols, such as methanol, ethanol, isopropanol, n-propanol and n-butanol; esters, such as ethyl acetate, isopropyl acetate, n-propyl acetate and n-butyl acetate; ketones, such as acetone and methyl ethyl ketone; ethers, such as tetrahydrofuran and dioxane; solubilized water, in other polar volatile solvents; and combinations thereof.

Certain propellant formulations for aerosol compositions of the antimicrobial formulations can also utilize alkanes, such as ethane, propane, n-butane, and isobutane; hydrofluoroalkanes, such as 1,1,1,2-tetrafluoroethane and 1,1,1,2,3,3,3-heptafluoropropane; ethers, such as dimethyl ether and methyl ethyl ether; and compressed gases, such as nitrogen, nitrous oxide, air, and carbon dioxide.

Specific examples of antimicrobial agents that are soluble in ethanol and isopropanol, preferably with the addition of lesser quantities of water, include, but are not limited to, poly(hexamethylene biguanide) and its salts, alexidine hydrochloride, chlorhexidine digluconate, chlorhexidine diacetate, glycerol monolaurate, benzalkonium chloride, benzethonium chloride, cetyltrimethylammonium chloride, cetylpyridynium chloride, alkyltrimethylammonium bromides, 1,2-octane diol, 2-ethylhexyl glycerin, gentian violet, silver salts, zinc salts, gentamicin sulfate, iodine, povidone-iodine, starch-iodine, neomycin sulfate, polymyxin B, bacitracin, mupirocin, tetracyclines, clindamycin, erythromycin, gentamicin, sodium fusidate, gramicidin, nitrofurazone, mafenide acetate, silver sulfadiazine, salicylates, terbinafine hydrochloride, miconazole nitrate, as well as ketoconazole, clotrimazole, itraconazole, metronidazole, salts thereof, and combinations thereof.

Some preferred antimicrobial agents include polymeric biguanides and polymeric bis(biguanides). Optionally, at least one low molecular weight bis(biguanide) or cationic or amphoteric surface active agent can be added as an additional antimicrobial agent. In some embodiments, a polymeric biguanide may include poly(hexamethylene biguanide) hydrochloride, a bis(biguanide) may include alexidine dihydrochloride or a chlorhexidine or its salts (e.g., chlorhexidine digluconate, chlorhexidine diacetate), and an amphoteric surfactant may include sodium N-lauryl-β-iminodipropionate. Combinations of polymeric antimicrobial biguanides with other antimicrobial agents may enhance efficacy against the opportunistic, pathogenic, microbial species.

In some embodiments, the polymeric biguanide is poly(hexamethylene biguanide) (PHMB), commercially available from Arch Chemicals, Inc., Smyrna, GA under the trademark Cosmocil™ CQ. Generally, the hexamethylene biguanide polymers are also referred to as poly(hexamethylene biguanide), poly(hexamethylene bisbiguanide) (PHMB), poly(hexamethylene guanide) (PHMB), poly(aminopropyl biguanide) (PAPB), poly[aminopropyl bis(biguanide)] (PAPB), polyhexanide and poly(iminoimidocarbonyl) iminohexamethylene hydrochloride. PHMB is the preferred abbreviation for this biocidal polymer. PHMB is a broad spectrum antimicrobial and has been used in contact lens multipurpose solutions, wound rinsing solutions, wound dressings, perioperative cleansing products, mouthwashes, surface disinfectant, food disinfectant, veterinary applications, cosmetic preservative, paper preservative, secondary oil recovery disinfectant, industrial water treatment, and in swimming pool cleaners. It is normally obtained commercially in the hydrochloride form in water and can be lyophilized to obtain a dry powder.

Examples of monoacyl glycerols include, but are not limited to, 1-O-decanoylglycerol (monocaprin), 1-O-undecanoylglycerol, 1-O-undecenoylglycerol, 1-O-dodecanoylglycerol (glycerol monolaurate, also called monolaurin and Lauricidine®), 1-O-tridecanoylglycerol, 1-O-tetradecanoylglycerol (monomyristin), 1-O-pentadecanoylglycerol, 1-O-hexadecanoylglycerol, 1-O-heptadecanoylglycerol, and 1-O-octanoylglycerol (monocaprylin). In general, glycerols acyl-substituted in the 1-O-position are more preferred than those substituted in the 2-O-position, or disubstituted in the 1-O and 2-O positions. Glycerol monolaurate is found in coconut oil and human breast milk, and it has been reported to inhibit the growth and toxin production by potentially pathogenic bacteria, particularly Gram-positive bacteria and is generally considered to be inactive with Gram negative bacteria (U.S. Pat. No. 5,804,549, and the references cited therein).

In some embodiments, the antimicrobial composition can also include a monoalkyl glycol and a monoalkyl glycerol. Such a product is available from Schülke & Mayr as Sensiva® SC10 and includes both 1,2-octanediol (a monoalkyl glycol) and 2-ethylhexyl glycerin (glycerol 1-(2-ethylhexyl) ether) (a monoalkyl glycerol), wherein such a combination is useful as a mild humectant and emollient with a unique skin feel. Additionally, it can contribute to the antimicrobial stability of cosmetic formulations by improving the efficacy of traditional cosmetic preservatives, such as parabens or phenoxyethanol.

The monoalkyl glycol can have a structure represented as follows:

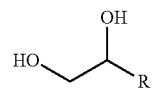

wherein $R=C_3-C_{18}$ branched or unbranched alkyl group or alkylene group. In some antimicrobial compositions, $R=C_3-C_{12}$ branched or unbranched alkyl group or alkylene group, or $R=C_3-C_8$ branched or unbranched alkyl group or alkylene group, or $R=C_3-C_8$ branched or unbranched alkyl group.

The monoalkyl glycerol (alternately referenced as a glycerol alkyl ether) can have a structure represented as follows:

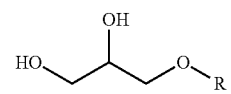

wherein $R=C_3-C_{18}$ branched or unbranched alkyl group or alkylene group. In some antimicrobial compositions, $R=C_6-C_{15}$ branched or unbranched alkyl group or alkylene group, or $R=C_7-C_{12}$ branched or unbranched alkyl group or alkylene group, or $R=C_7-C_{12}$ branched or unbranched alkyl group.

In some embodiments, the antimicrobial compositions can include one or more additional surfactants to effect lowering of the surface tension of the liquid composition in order to facilitate flow of the liquid composition into skin folds and crevices. In some embodiments, the surfactant can facilitate release of the antimicrobial agents from the polymer coating, particularly in aqueous environments. Suitable surfactants include, but are not limited to, cationic, anionic, nonionic, amphoteric and ampholytic surfactants. In some embodiments, surfactants are nonionic and amphoteric surfactants because of their lower complexation or coordination with a cationic antimicrobial agent. Suitable nonionic surfactants include the ethylene oxide/propylene oxide block copolymers of poloxamers, reverse poloxamers, poloxamines, and reverse poloxamines. Poloxamers and poloxamines are available from BASF Corp. under the trade names of Pluronic® and Tetronic®, with a preference to Pluronic F38, Pluronic F68, and Pluronic F127. Other nonionic surfactants include, but are not limited to, polyethylene glycol esters of fatty acids, e.g., coconut, polysorbate, polyoxyethylene or polyoxypropylene ethers of higher alkanes ($C_{12}-C_{18}$), polysorbate 20 available under the trademark Tween 20, polyoxyethylene (23) lauryl ether available under the trademark Brij 35, polyoxyethyene (40) stearate available under the trademark Myrj 52, and polyoxyethylene (25) propylene glycol stearate available under the trademark Atlas G 2612, all available by Akzo Nobel, Chicago, IL. Other neutral surfactants include nonylphenol ethoxylates such as nonylphenol ethoxylates, Triton X-100, Brij surfactants of polyoxyethylene vegetable-based fatty ethers, Tween 80, decyl glucoside, and lauryl glucoside, and the like.

Suitable amphoteric surfactants include, but are not limited to, sodium N-lauryl-β-iminodipropionate, sodium lauriminodipropionate, disodium lauriminodipropionate, disodium 3,3'-(dodecylimino)dipropanoate, disodium 3-[2-carboxylatoethyl(dodecyl)amino]propanoate, disodium lauroamphodiacetate, sodium-2-ethylhexyliminodipropionate, disodium cocoamphodiacetate, sodium cocoamphoacetate, ammonium lauriminodipropionate, triethanolamine lauraminopropionate, disodium cocaminodipropionate, cocamidopropyl betaine, lauramidopropyl betaine, cocobetaine, laurylbetaine, isostearamidopropyl betaine, cocamidopropyl hydroxysultaine, lauramidopropyl hydroxysultaine, disodium capryloamphodiacetate, sodium lauroamphoacetate, sodium cocaminodipropionate, ammonium cocaminodipropionate, triethanolamine lauriminodipropionate, sodium cocoamphohydroxypropylsulfonate, sodium cocoamphopropionate, sodium cornamphopropionate, sodium lauroamphohydroxypropylsulfonate, sodium lauroamphopropionate, ammonium cocaminopropionate, ammonium cocoamphoacetate, disodium caproamphodiacetate, disodium caproamphoadipropionate, disodium capryloamphodiacetate, disodium capryloamphodipriopionate, disodium cocoamphocarboxyethylhydroxypropylsulfonate, disodium laureth-5 carboxyamphodiacetate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, cocoamidopropyldimethylglycine, cocoamphocarboxypropionate, cocamidopropyl PG-dimonium chloride phosphate, oleamidopropyl betaine, myristamidopropyl betaine, dimethicone propyl PG-betaine, palmitamidopropyl betaine, undecylenamidopropyl betaine, combinations thereof, and the like. Sodium-N-lauryl-β-iminodipropionate (also called sodium N-dodecyliminodipropionate, disodium lauriminodipropionate, disodium 3,3'-(dodecylimino)dipropanoate, disodium 3-[2-carboxylatoethyl(dodecyl)amino] propanoate) is an exemplary amphoteric surfactant for use in the antimicrobial compositions described herein. It is commercially available from BASF Corporation as Deriphat® 160C in the monosodium salt form.

Sunscreens are widely used as a lotion, spray, gel or other topically-applied product that absorb or reflect the sun's ultraviolet radiation on exposed skin, and thus help protect against sunburn and potential blister formation. It is believed that sunburn and/or blister formation may facilitate infection from opportunistic pathogens. Active ingredients of sunscreens are divided into chemical versus physical sun blocking agents, wherein chemical sun-blocking agents absorb the energy of UV radiation while physical sun-blocking agents reflect or scatter UV radiation before it reaches the skin. The primary types of physical sun-blocking agents are zinc oxide and titanium dioxide, both of which are insoluble inorganic materials. Both zinc oxide and titanium dioxide provide broad spectrum UVA (320-400 nanometers) and UVB (290 to 320 nanometers) protection and are gentle to skin. The use of physical sun-blocks may cause a sun-blocking composition to be opaque or translucent. Chemical sun-blocking agents, however, may be solubilized and added to a sunscreen formulation that results in a transparent or translucent coating on skin. The efficiency of a sunscreen is measured by its sun protection factor, or SPF, wherein SPF indicates how long it will take for UVB rays to redden skin when using a sunscreen, compared to how long skin would take to redden without the product.

In some embodiments, hydrophobic sunscreen agents are incorporated into the water-insoluble polymer coating on skin or tissue because of their lower water solubility and extended time for diffusion from the polymer coating when in an aqueous environment. In some embodiments, the hydrophobic, water-insoluble sunscreen components are selected from, but are not limited to, avobenzone (butyl-methoxydibenzoylmethane; 4-tert-butyl-4'-methoxydibenzoylmethane), homosalate (homomenthyl salicylate; 3,3,5-trimethylcyclohexyl 2-hydroxybenzoate), octisalate (octyl salicylate; 2-ethylhexyl salicylate; 2-ethylhexyl 2-hydroxybenzoate), octocrylene (2-ethylhexyl-2-cyano-3,3-diphenyl-2-acrylate; 2-ethylhexyl-2-cyano-3,3-diphenyl-2-propenoate), oxybenzone (benzophenone-3; (2-hydroxy-4-methoxyphenyl)phenylmethanone; 2-hydroxy-4-methoxybenzophenone), otinoxate (ethylhexyl methoxycinnamate; octyl methoxycinnamate), and combinations thereof. Avobenzone absorbs in the UVA, homosalate absorbs in the UVB, octisalate absorbs in the UVB, octocrylene absorbs in the UVB, oxybenzone absorbs in the UVA and UVB, and otinoxate absorbs in the UVB. In order to slow the photodegradation of avobenzone and otinoxate, photostabilizers can be added, such as Polysilicone-15 (polydimethylsiloxane-based oligomeric UV absorber), undecylcrylene dimethicone, diethylhexyl-2,6-naphthalate, ethylhexyl methoxycrylene, and the like.

In outdoor environments, insect repellents are often used to reduce the incidence of insect bites and stings, which can be vectors for a disease entering a host. Some of the most widely used ingredients in insect repellent sprays are N,N-diethyl-3-methylbenzamide or N,N-diethyl-m-toluamide, commonly referred to as DEET, and essential oils. In some embodiments the antimicrobial composition can include insect repellents of natural origin, such as oil of lemon eucalyptus, with its active ingredient p-menthane-3,8-diol, lemongrass oil, citronella oil, castor oil, cedar oil, clove oil, geraniol oil, peppermint oil, eucalyptus oil, pine oil, rosemary oil, cedarwood oil, lavender oil, spearmint oil, lime oil, bog myrtle, neem oil and soybean oil, potentially in combination with an amido insect repellent such as picaridin (icaridin, hydroxyethyl isobutyl piperidine carboxylate). Picaridin is a synthetic compound developed from a plant extract from the plant genus that produces table pepper.

In addition to essential oils acting as insect repellents, in some embodiments other essential oils can also be added to the formulation as fragrance or aromatic agents, and/or as antimicrobial agents, including thymol, menthol, sandalwood, camphor, cardamom, cinnamon, jasmine, juniper, menthol, lemon, rose, orange, oregano, mint, linalool, bergamot, cypress, nutmeg, spruce, tea tree, wintergreen (methyl salicylate), vanilla, and the like. In some embodiments, essential oils include thymol, sandalwood oil, wintergreen oil, eucalyptol, and pine oil.

In some embodiments, emollients can be added to the antimicrobial compositions to provide a more soothing skin feel, said emollients are selected from petrolatum, lanolin, mineral oil, dimethicone, siloxy compounds, isopropyl palmitate, isopropyl myristate, isopropyl isostearate, isostearyl isostearate, diisopropyl sebacate, propylene dipelargonate, 2-ethylhexyl isononoate, 2-ethylhexyl stearate, cetyl lactate, lauryl lactate, isopropyl lanolate, 2-ethylhexyl salicylate, cetyl myristate, oleyl myristate, oleyl stearate, oleyl oleate, hexyl laurate, isohexyl laurate, lanolin, olive oil, cocoa butter, shea butter, octyldodecanol, hexyldecanol, dicaprylyl ether, decyl oleate, and combinations thereof. In some embodiments, the concentration of emollients in the antimicrobial polymer solution is 0 to 5 wt-%, or from 0.1 to 5 wt-%.

In some embodiments, skin care additives, polymer film flexibilizers, plasticizers, and compatibilizers can be added for enhancing the performance of the antimicrobial composition when applied to a human or animal host, with a concentration in the antimicrobial solution of from 0 to 5 wt-%, or from 0.1 to 5 wt-%.

Because many antimicrobial agents are polar in nature, their solubility and compatibilization in a formulation is enhanced in polar solvents, such as, ethanol and isopropanol, which can include a lesser amount of solubilized water. Such alcohols also have innate biocidal activity. Examples of polar antimicrobial agents that have solubility in ethanol and isopropanol, potentially with lower volumes of water, include, but are not limited to, poly(hexamethylene biguanide) hydrochloride and other salts, chlorhexidine digluconate, chlorhexidine diacetate, alexidine dihydrochloride, silver salts, benzalkonium chloride, 1,2-octane diol, 2-ethylhexyl glycerin, benzethonium chloride, gentamicin sulfate, iodine, povidone-iodine, starch-iodine, neomycin sulfate, polymyxin B, bacitracin, tetracyclines, clindamycin, gentamicin, nitrofurazone, mafenide acetate, silver sulfadiazine, terbinafine hydrochloride, miconazole nitrate, as well as ketoconazole, clotrimazole, itraconazole, metronidazole, antimicrobial peptides, polyquaternium-1, polyquaternium-6, polyquaternium-10, cationic guar, and water-soluble derivatives of chitosan, and the like, and combinations thereof. In some embodiments, the antimicrobial agents can be selected from poly(hexamethylene biguanide) and its salts, glycerol monolaurate, alexidine hydrochloride, chlorhexidine, chlorhexidine digluconate, chlorhexidine diacetate, benzethonium chloride, and mixtures thereof.

In some embodiments, prior to solvent evaporation, the liquid coating material can include about 0.10 to 50.0 wt-% of a polymer dissolved in about 45.0 to 99.7 wt-% of a volatile polar and/or nonpolar liquid as part of a solvent system. In some embodiments, water can be added as a cosolvent for antimicrobial agents, particularly those in salt form, preferably at a concentration less than 4.0 wt-%, or less than 3 wt-%, or less than 2 wt-%, or less than 1 wt-%.

In some embodiments, the polymer may be a film-forming polymer that is adhesive to skin, tissue and mucous membranes.

In other embodiments, the polymer can include at least one polymerizable hydrophobic vinyl-type monomer. In some embodiments, the polymer includes at least one hydrophilic vinyl-type monomer can be added. The arrangement of at least one polymerizable hydrophobic vinyl-type monomer and at least one hydrophilic vinyl-type monomer can enhance the interaction of the subsequent polymer coating with other active agents, modulating their compatibility and their release rate from the polymer coating.

In some embodiments, the antimicrobial liquid composition can contain a polymeric biguanide, at a concentration of from 0.10 wt-% (1,000 ppm) to 1.0 weight % (10,000 ppm), or from 0.25 wt-% (2,500 ppm) to 0.75 wt-% (7,500 ppm), or from or from 0.40 wt-% (4,000 ppm) to 0.60 wt-% (6,000 ppm). In some embodiments, the antimicrobial liquid composition can include at least one additional antimicrobial agent at a concentration of from 0.10 wt-% (1,000 ppm) to 4.0 wt-% (40,000 ppm), or from 0.15 wt-% (1,500 ppm) to 3.0 wt-% (30,000 ppm), or from 0.5 wt-% (5,000 ppm) to 2.0 wt-% (10,000 ppm).

In some embodiments, after solvent evaporation, the dry polymer coating composition can include up to 99.5% film-forming polymer composition; a polymeric biguanide at a concentration of from 0.30 wt-% (4,000 ppm) to 10.0 wt-% (100,000 ppm), or from 1.0 wt-% (10,000 ppm) to 7.5 wt-% (75,000 ppm), or from or from 2.0 wt-% (20,000 ppm) to 5.0 wt-% (50,000 ppm); and at least one additional antimicrobial agent at a concentration of from 0.20 wt-% (2,000 ppm) to 10.0 wt-% (100,000 ppm), or from 0.60 wt-% (6,000 ppm) to 7.5 wt-% (40,000 ppm), or from 0.75 wt-% (7,500 ppm) to 5.0 wt-% (50,000 ppm).

In some embodiments, the surfactant can be present in the liquid antimicrobial composition at a concentration of from 0.01 wt-% (100 ppm) to 1.0 wt-% (10,000 ppm), or from 0.10 wt-% (1,000 ppm) to 0.75 wt-% (7,500 ppm), or from 0.40 wt-% (4,000 ppm) to 0.60 wt-(60,000 ppm). The surfactant lowers the surface tension of the solution, facilitating flow into skin crevices and skin folds, and may contribute to enhancing overall antimicrobial behavior. In the dried antimicrobial polymer coating, the surfactant can be present from 0.04 wt-% (400 ppm) to 4.0 wt-% (40,000 ppm), or from 0.40 wt-% (4,000 ppm) to 3.0 wt-% (30,000 ppm), or from 1.0 wt-% (10,000 ppm) to 2.0 wt-% (20,000 ppm).

In some embodiments, a method of inhibiting or preventing pathogenic microbial infection is provided. The method can include applying a liquid antimicrobial polymer coating formulation according to any of the variants described herein to a biological surface, and evaporating said solvent. The applying and evaporating steps can occur prior to engaging in an activity where the biological surface could come into contact with a potential source of a pathogenic microbial infection.

Examples of such activities include, but are not limited to, boating, fishing, swimming, wading, working, backpacking, cycling, camping, canoeing, canyoning, caving, cooking, golfing, hiking, horseback riding, hunting, kayaking, lounging, mountaineering, mountain biking, parasailing, photography, racing, rafting, reading, rock climbing, running, sailing, seafood handling, sightseeing, skateboarding, skiing, skimboarding, snowboarding, sledding, sunning, surfing, trekking, walking, water skiing, including all water and other sport, recreational, and work-related activities. Such activities also include, but are not limited to, activities that can result in insect, animal, fish, leech, mite, tick, spider, flea, and mosquito bites, parasitic infestations, ant stings, bee stings, stonefish stings, jellyfish stings, sunburn, skin abrasions, skin lesions, burns, skin lacerations, skin punctures, skin tears, and the like that facilitate microbial infection.

In some embodiments, the applying step comprises application by at least one of spraying, wiping, dipping, painting, brushing, casting, and aerosolization.

In some embodiments, a kit for of inhibiting or preventing pathogenic microbial infection is provided. The kit can include a liquid antimicrobial polymer coating formulation according to any of the variants described herein, as well as, instructions for using the liquid antimicrobial polymer coating formulation. The instructions can include applying the liquid coating formulation to the skin prior to engaging in an activity where the skin could come into contact with a potential source of a pathogenic microbial infection. In some embodiments, the instructions include reapplication of the liquid coating formulation at defined intervals. The defined intervals can be the passage of a discrete periods of time, engaging in a specific activity (e.g., swimming), or a combination thereof.

As used herein, "inhibition" has its standard meaning and includes limiting, preventing, or blocking an action or function, particularly of exogenous microorganisms.

As used herein, "exogenous" bacteria has its standard meaning and includes microorganisms introduced to a host from the external world, particularly from aquatic and terrestrial environments, as well as from the atmosphere.

As used herein, "necrotizing" has its standard meaning and includes causing the death of tissue.

As used herein, "necrotizing fasciitis" has its standard meaning and includes severe bacterial infection of the fascia, causing inflammation of the tissues that line and separate muscles, causing extensive tissue death.

As used herein, "fascia" has its standard meaning and includes a flat band of tissue below the skin that covers underlying tissues and separates different layers of tissue. Fascia also encloses muscles.

As used herein, "erythema" has its standard meaning and includes a superficial reddening of the skin, usually in patches, as a result of injury or irritation, causing dilatation of the blood capillaries.

As used herein, "infection" has its standard meaning and includes the invasion and multiplication of microorganisms such as bacteria, viruses, and parasites that are not normally present within the body resulting in the establishment of a pathogen in its host after invasion. Microorganisms that live naturally in the body are not considered infections.

As used herein, "inflammation" has its standard meaning and includes a localized reaction that produces redness, warmth, swelling, and pain as a result of infection, irritation, or injury. Inflammation can be external or internal.

As used herein, an "antimicrobial agent" has its standard meaning and includes a substance that kills microorganisms or inhibits their growth or replication.

As used herein, "biologically-active agent" has its standard meaning and includes chemical substances or formulations that beneficially affect humans, animals, or plants or is intended for use in the cure, mitigation, treatment, prevention, or diagnosis of infection or disease, or is destructive to or inhibits the growth of microorganisms.

As used herein, "pathogen" has its standard meaning and includes a bacterium, virus, or other microorganism that can cause disease.

As used herein, "opportunistic pathogen" has its standard meaning and includes an infectious microorganism, such as bacteria, virus, fungi or protozoa, which can cause disease when the host's resistance is low or compromised, such as by occurrence of a wound, medication, prior infection, immunodeficiency, and ageing.

As used herein, "commensal" has its standard meaning and includes a form of symbiosis between two organisms of different species where one microorganism benefits from the association, whereas the other is largely unaffected or not significantly harmed or benefiting from the relationship.

As used herein, "virulence" has its standard meaning and refers to the degree of pathogenicity, the relative ability of a microorganism to cause disease.

As used herein, "pathogenicity" has its standard meaning and includes the ability to produce disease in a host organism.

As used herein, "symbiont" has its standard meaning and includes an organism living in a state of symbiosis with another organism.

As used herein, "zoonotic" has its standard meaning and includes zoonosis, a disease that can be transmitted from animals to people, particularly a disease that normally exists in animals but that can infect humans.

As used herein, "genera" has its standard meaning and includes the major subdivision of a family or subfamily in the classification of organisms, usually consisting of more than one species.

As used herein, "skin tears" has its standard meaning and includes traumatic wounds that result from a separation of the epidermis and the dermis.

As used herein, "puncture" has its standard meaning and includes an injury that is caused by a pointed object that pierces or penetrates the coating or skin.

As used herein, "insect repellent" has its standard meaning and includes a composition that repels insects.

As used herein, "essential oil" has its standard meaning and includes natural hydrophobic oil containing volatile aroma compounds from a plant, having the characteristic fragrance of the plant or other source from which it is extracted.

As used herein, "sunscreen" has its standard meaning and includes a substance or formulation that prevents sunburn, skin cancers, blisters, and other skin conditions caused by exposure to the sun, by adsorbing and reflecting ultraviolet radiation.

As used herein, "emollient" has its standard meaning and includes a composition or preparation that soothes the skin, such as a moisturizer, cream, lotion, oil, rub, salve, unguent, or balm.

As used herein, a compound or polymer is "soluble" or "solubilized" if the amount of compound or polymer present in the solvent system is completely dissolved in the solvent system without forming a precipitate or visible, swollen gel particles in solution.

As used herein, "polymer coating" has its standard meaning and includes a polymer that is capable of forming an adhesive, coherent film on a biological surface.

As used herein, "aqueous" has its standard meaning and includes a spectrum of water-based solutions including, but not limited to, homogeneous solutions in water with solubilized components, emulsified solutions in water stabilized by surfactants or hydrophilic polymers, and viscous or gelled homogeneous or emulsified solutions in water.

As used herein, "hydrophilic" has its standard meaning and includes compounds that have an affinity to water and can be ionic or neutral or have polar groups in their structure that attract water. For example, hydrophilic compounds can be miscible, swellable, gelled, or soluble in water.

As used herein, "hydrophobic" has its standard meaning and includes repelling water, being insoluble or relatively insoluble (i.e., <5% soluble) in water, and lacking an affinity for water.

As used herein, "amphoteric" has its standard meaning and includes a mixture of cationic and anionic charges on a molecule or polymer in which the overall charge is locally pH dependent.

As used herein, "ampholytic" has its standard meaning and includes an equal number of cationic and anionic charges on a molecule or polymer.

As used herein, "volatile" has its standard meaning, that is, it can evaporate rapidly at normal temperatures and pressures. For example, a solvent is volatile if one drop (0.05 mL) of the solvent will evaporate completely between 20-25° C. within 5 minutes, or within 4 minutes, or within 3 minutes, or within 2 minutes, or within 1 minute, or within 30 seconds, or within 15 seconds.

As used herein, a "biocide" has its standard meaning and includes an antimicrobial substance that can deter, hinder, inhibit, render harmless, exert a controlling effect, reduce, kill, eradicate, or eliminate any harmful microorganism.

As used herein, a "Log Reduction" has its standard meaning and includes a 10-fold (one decimal) or 90% reduction in numbers of live microorganisms.

EXAMPLES

The following ingredients and their abbreviations are used in this invention:
- ACR: Acrylate Copolymer, octylacrylamide/acrylates/butylaminoethyl methacrylate copolymer, MakingCosmetics Inc., lot 1131328.
- ALEX: Alexidine Dihydrochloride, Toronto Research Chemicals, lot 4-WG-119-2.
- AVO: Avobenzone, Merck, lot 5844G1243313.
- BZC: Benzethonium Chloride, Sigma, lot SLBC7904V.
- CHG: Chlorhexidine gluconate, Spectrum Chemicals, lot ZQ1023.
- DER: Sodium N-Lauryl-β-iminodipropionate, Deriphat® 160C, BASF Corp., lot 7518575.
- EtOH: SDA 40B, Special Denatured Alcohol, Warner Graham, lot 2693L1.
- GML: Glycerol Monolaurate, Lauricidin®, Med-Chem Laboratories, lot 4010608422.
- HEMA: 2-Hydroxyethyl Methacrylate, Monomer-Polymer, lot 23-77-19
- HMS: Homosalate, EMD Chemicals Inc., lot 2363.
- OCTC: Octocrylene, Merck, lot 5377E140.
- OCTS: Octisalate, EMD Chemicals Inc., lot 2137.
- OLE: Oil of Lemon Eucalyptus, Citriodiol®, Citrifine International, lot 123391104.
- PHMB: Poly(hexamethylene biguanide hydrochloride), Cosmocil™ CQ, Arch Chemical, lot 11RC116995.
- PVBI: Poly(vinyl acetate-co-butyl maleate-co-isobornyl acrylate), Sigma Aldrich, lot 05928PG
- SC10: 1,2-Dihydroxyoctane and 2-Ethylhexyl Glycerin, Sensiva® SC 10, Schülke & Mayr, lot 1178933.
- TRIS:HEMA: copolymer of 2.5:1 mole ratio of TRIS and HEMA (U.S. patent application Ser. No. 14/046,591).
- TRIS: 3-[Tris(trimethylsiloxy)silyl]propyl Methacrylate, Silar, lot 072513
- VP/E: VP/Eicosene copolymer (N-vinylpyrrolidone and 1-eicosene), Ganex® V-220F, Ashland Inc., lot 012298247.

General Formulation Procedures:
Preparation of Antimicrobial Polymer Compositions The film-forming polymer selected was dissolved in denatured alcohol (SDA 40B) at 20 wt-% (Solution A). PHMB in a 20 wt-% water solution and at least one additional antimicrobial agent, such as glycerol methacrylate, in denatured ethanol were adjusted in ethanol content (Solution B) such that when Solutions A and B were mixed, the compositions shown in the following Tables pertain to the polymer utilized, ethanol (denatured ethanol), water, PHMB, and GML (glycerol monolaurate) concentrations obtained (Solution C).

Preparation of Antimicrobial Polymer Compositions with Sunscreen Additives

To Solution C was added an appropriate amount of avobenzone (AVO), homosalate (HMS), octisalate (OCTS), and octocrylene (OCTC) in denatured ethanol such that the antimicrobial sunscreen formulation (Solution D) contained approximately 3.0% avobenzone, 10% homosalate, 5.0% octisalate, 3.5% octocrylene and 10 wt-% polymer.

Preparation of Antimicrobial Polymer Compositions with Insect Repelling Agents

When sunscreen additives were admixed with an insect repelling agent, a procedure analogous to Solution D was utilized, with the addition of approximately 2.5 wt-% of oil of lemon eucalyptus (OLE), such that the final polymer concentration was 10 wt-% and the sunscreen compositions were as reported above. Without sunscreen additives, 2.5 wt-% of oil of lemon eucalyptus was used in a process similar to that of Solution C.

Preparation of Antimicrobial Polymer Compositions with Sunscreen and Other Additives To a procedure similar to the preparation of Solution D was added one or more other agents selected from other antimicrobial agents, surfactants, and emollients, including DER (Deriphat® 160C, sodium N-lauryl-β-iminodipropionate), and SC10 (Sensiva® SC 10, 1,2-dihydroxyoctane and 2-ethylhexyl glycerin), BZC (Benzethonium Chloride), CHG (chlorhexidine gluconate), and ALEX (alexidine dihydrochloride), with an overall polymer concentration of approximately 10 wt-%.

Zone of Inhibition:

Zone of Inhibition (ZOI) analysis for antimicrobial effectiveness against opportunistic pathogenic microorganisms was conducted by the following procedure: The test organism strains were *Vibrio vulnificus*, ATCC #27562, isolated in Florida as a pathogen from human blood; *Streptococcus pyogenes*, ATCC #BAA-1411, clinical respiratory specimen (Canada); and *Escherichia coli*, ATCC #8739, from feces and commonly used as quality control strain. *Vibrio vulnificus* was grown in marine broth medium (MBM) as a suspension and on Marine Agar Medium (MAM) spread plates for ZOI assays. The other organisms were grown in Tryptic Soy Broth (TSB) or on Tryptic Soy Agar (TSA) spread plates. After bacteria were spread onto the surfaces of the agar plates to create a lawn, the test antimicrobial compositions and negative base formulation controls (without antimicrobial components) were placed on duplicate plates, using cloning cylinders to control the location of the delivered test or control materials. The plates were incubated at 37° C. with ZOIs monitored, photographed and measured for up to 4 days after set-up.

The 150 mm agar plates (TSA for *Streptococcus pyogenes* and *Escherichia coli*; MAM for *Vibrio vulnificus*) were labeled for inoculation (total N=4 plates). The test organisms were grown overnight in their appropriate broth and the optical density (OD) values were read. Each was diluted to 0.1 or 0.2 OD600 unit and 1 ml was spread on each of the plates. The plates were allowed to dry for 20 min. The cloning cylinders were placed on the plate in a spread out pattern and 20 µl of each test substance was pipetted into the cloning cylinder rings used to guide the liquid onto the set areas of comparable size. The Test negative control (20 µl) was a base polymer formula solution without active ingredients. Plates were observed for bacterial growth inhibition for up to four days. They were photographed, and the Zones of Inhibition were measured, averaged, and recorded on spreadsheets.

Log Reduction (Limiting Dilution):

Log Reduction data for various antimicrobial compositions towards several opportunistic pathogens were conducted by the following procedure, wherein log kill data are described below in terms of the test organism species studied, strain, ATCC #, description of the organism, and the media used, which included Marine Broth Medium (MBM), Marine Agar Medium (MAM), Tryptic Soy Broth (TSB), and Tryptic Soy Agar (TSA).

Gram Negative Bacteria

*Vibrio vulnificus*: ATCC #27562; Water pathogen; isolated in Florida as a pathogen from human blood; media of MBM, MBA.

*Pseudomonas aeruginosa*: ATCC #27853: Blood culture isolation; Boston 41501; media of TSB, TSA.

Gram Positive Bacteria

*Staphylococcus aureus*: MRSA: ATCC #700787: Methicillin resistant *S. aureus*: media of TSB, TSA.

*Streptococcus pyogenes*: ATCC # BAA-1411: Clinical respiratory specimen (Canada)—TSB, TSA.

Yeast (Fungi)

*Candida albicans*: ATCC #10231; Pathogenic yeast; media of TSB, TSA.

*Vibrio vulnificus* was grown in MBM as a suspension and on MAM culture plates. The other organisms were grown in TSB as a suspension and on TSA culture plates. Test organisms were grown in liquid broth cultures overnight; optical densities (ODs) were read and used to determine bacterial dilutions for preparing the plates for the assay. After 24 hr growth the OD readings were assayed at 600 nm to determine relative cell numbers. A separate 96-well plate was set up for each organism (N=5). The plates were coated with the antimicrobial compositions and the Negative control solutions (40 µl per well overnight binding and evaporation). Culture suspensions were adjusted to a working concentration of 0.1 OD600, followed by six (6) ten-fold serial dilutions (indicated as d1-d7) in a 96-well dilution plate. Each well was loaded with 200 µL. From previous work, the bacterial cell count was determined to be approximately $10^8$ CFU/ml.

After 48 hr, four methods were used to analyze microbial growth:

a) All wells were scored for visible growth.

b) All plates were read on a plate reader at 600 nm as a measure of growth and graphed.

c) A ResBlue assay was done to assess sample viability and re-growth from a transferred 50 µL volume from each well to 100 µL culture broth containing ResBlue. Data was captured for all wells on a microplate reader as absorbance at 570 nm at 2 and 4 hr for all tests and controls. The 4 hr time point was used because the 2 hr time point was too short to get a reading from the ResBlue assay from smaller numbers of organisms and was not used for the calculations. Quadruplicate culture wells were analyzed for Mean+SD values.

d) A 10 µL drop was run down an agar plate at the highest dilutions so that colonies could be counted and growth inhibitory concentrations quantified.

All wells were scored for visible growth and OD600 readings were taken after 48 hr. Log-fold reduction was calculated based on the starting concentration of 108 organisms in the tests.

Table 1 presents the preparations of water-insoluble, antimicrobial, film-forming polymer solutions utilizing three film-forming polymers and the antimicrobial combination of poly(hexamethylene biguanide) hydrochloride (PHMB) and glycerol monolaurate (GML) in denatured ethanol (EtOH) with a low concentration of water, which also include additives of the ampholytic surfactant DER (sodium N-lauryl-β-iminodipropionate, Deriphat® 160C) and the deodorant-based Gram positive antimicrobial emollient Sensiva® SC10. The compositions include liquid polymer containing formulations (Examples 1-6) and dried polymer films (Examples 1a-6a) formed from those liquid formulations.

The film-forming polymers are two commercial film-forming polymers of poly(vinyl acetate-co-butyl maleate-co-isobornyl acrylate) (PVBI) from Sigma-Aldrich, and N-vinylpyrrolidone/eicosene copolymer (VP/E) from Ashland Inc., as well as a polymer of 2.5:1 mole % ratio of the monomer TRIS (3-methacryloyloxypropyltris (trimethylsiloxy)silane) with HEMA (2-hydroxyethyl methacrylate) (TRIS:HEMA) (prepared according to U.S. patent application Ser. No. 14/046,591). For all formulations, the concentration of polymer in solution was approximately 10 wt-%, while that of PHMB and GML were each approximately 0.5 wt-%. For the samples dried of solvent (denatured ethanol and water), the polymer concentrations were approximately 90 wt-% and the PHMB and GML concentrations in the polymer film were approximately 4 wt-%. When DER was incorporated in solution, its concentration in solution was approximately 0.1 wt-%, while in the dried polymer film its concentration was approximately 0.9 wt-%; when the deodorant-based Gram positive antimicrobial emollient Sensiva® SC10 was added in solution at 0.3 wt-%, the dry polymer composition contained SC10 at approximately 2 wt-%. The dried polymer films of Samples 1a, 2a, 3a, 4a, 5a, and 6a were cast on glass slides and were smooth and uniform with no pin-holes. The films were transparent to mildly translucent, adherent, and water-insoluble. The preparation of Sample 3 was slightly different than Samples 1, 2, 4, 5, and 6 in that the VP/E copolymer was warmed into the denatured ethanol solution, creating a homogeneous cream. Casting of this cream, with the added antimicrobial agents, gave a waxy, translucent, pin-hole free homogeneous film. The polymer solution of Sample 6 was a stable mixture of polymers of PVBI and TRIS:HEMA, and that of the dried polymer film (Sample 6a) had similar properties to Samples 1a, 2a, 4a, and 5a.

TABLE 1

Antimicrobial Film-forming Polymer Compositions

| Sample | PVBI | TRIS:HEMA | VP/E | EtOH | Water | PHMB | GML | DER | SC10 |
|---|---|---|---|---|---|---|---|---|---|
| 1 | 9.92 | 0 | 0 | 87.29 | 1.82 | 0.46 | 0.51 | 0 | 0 |
| 1a | 91.09 | 0 | 0 | 0 | 0 | 4.23 | 4.68 | 0 | 0 |
| 2 | 0 | 10.11 | 0 | 87.15 | 1.80 | 0.45 | 0.49 | 0 | 0 |
| 2a | 0 | 91.49 | 0 | 0 | 0 | 4.07 | 4.44 | 0 | 0 |
| 3 | 0 | 0 | 10.00 | 87.20 | 1.84 | 0.46 | 0.50 | 0 | 0 |
| 3a | 0 | 0 | 91.24 | 0 | 0 | 4.20 | 4.56 | 0 | 0 |
| 4 | 0 | 10.00 | 0 | 86.94 | 2.00 | 0.46 | 0.50 | 0.10 | 0 |
| 4a | 0 | 90.42 | 0 | 0 | 0 | 4.16 | 4.52 | 0.90 | 0 |
| 5 | 0 | 10.00 | 0 | 86.63 | 2.03 | 0.46 | 0.49 | 0.09 | 0.30 |
| 5a | 0 | 88.18 | 0 | 0 | 0 | 4.06 | 4.32 | 0.79 | 2.65 |
| 6 | 5.00 | 5.00 | 0 | 87.20 | 1.84 | 0.46 | 0.50 | 0 | 0 |
| 6a | 45.62 | 45.62 | 0 | 0 | 0 | 4.20 | 4.56 | 0 | 0 |

In Table 2 are presented sustained release zone of inhibition (ZOI) data over a three and six day period for film Samples 1a and 2a, cast from the respective solutions (Samples 1 and 2) and spread on Marine Agar Medium and tested against the opportunistic pathogen Vibrio vulnificus (ATCC #27562). The polymer films were therefore composed of either PVBI with PHMB and GML (Sample 1a) or TRIS:HEMA with PHMB and GML (Sample 2a). The negative control was commercial Acrylate Copolymer (ACR) (octylacrylamide/acrylates/butylaminoethyl methacrylate) from MakingCosmetics Inc., dried from denatured ethanol solution, which had no ZOI. Table 2 demonstrates that a water-insoluble polymer film containing the antimicrobial agents of PHMB and GML is effective against the opportunistic pathogen, Vibrio vulnificus. It is seen that the sustained release of PHMB and GML was slightly greater for the TRIS:HEMA copolymer (Sample 2a), possibly due to residual carboxylic acid functional groups of the polymer of Sample 1a or to a greater hydrophobicity of its polymer film. The biocidal activity is believed to result from a diffusion of the antimicrobial agents at the interface of the polymer coating with the aqueous medium.

TABLE 2

Sustained Release ZOI for Samples 1a, 2a with Vibrio vulnificus

| Sample | ZOI V. vulnificus (cm²) | |
|---|---|---|
| | 72 hr | 144 hr |
| 1a | 1.30 | 1.30 |
| 2a | 1.50 | 1.40 |

TABLE 3

Sustained Release ZOI for Sample 5a with S. pyogenes, E. coli, and V. vulnificus

| | ZOI S. pyogenes (cm²) | | | ZOI E. coli (cm²) | | | ZOI V. vulnificus (cm²) | | |
|---|---|---|---|---|---|---|---|---|---|
| Sample | 24 hr | 48 hr | 72 hr | 24 hr | 48 hr | 72 hr | 24 hr | 48 hr | 72 hr |
| 5a | 0.63 | 0.63 | 0.58 | 0.21 | 0.21 | 0.26 | 0.45 | 0.55 | 0.65 |

The preparation of a polymer-based antimicrobial sunscreen solution (Sample 7) and dried composition (Sample 7a) is presented in Table 4 with a negative control, using four sunscreen additives, for use in determining log reduction of several opportunistic pathogens (Table 5). The four sunscreen additives include AVO (avobenzone), HMS (homosalate), OCTS (octisalate), and OCTO (octocrylene). These sunscreen components are projected to give an SPF value of approximately 50, with UVA and UVB radiation protection. The dried composition of Sample 7a contained the TRIS:HEMA polymer at a concentration of 30 wt-%, substantially less than those of Samples 2a, 4a, and 5a in Table 1 for TRIS:HEMA, the four sunscreen agents at a concentration of 66 wt-%, the antimicrobial agents PHMB and GML at a concentration approximately one-third those given in Table 1 for Sample 5a, and the DER surfactant and antimicrobial emollient SC10 concentrations at above 1 wt-%.

TABLE 4

Antimicrobial Sunscreen Compositions for Log Kill

| Solution | Composition, wt % | | | | | | | | | | |
|---|---|---|---|---|---|---|---|---|---|---|---|
| | T:H 2.5:1 | EtOH | Water | AVO | HMS | OCTS | OCTO | PHMB | GML | DER | SC 10 |
| 7 | 9.90 | 65.19 | 1.80 | 3.00 | 10.30 | 5.00 | 3.50 | 0.40 | 0.50 | 0.10 | 0.31 |
| 7a | 30.00 | 0 | 0 | 9.09 | 31.20 | 15.15 | 10.60 | 1.21 | 1.51 | 0.30 | 0.94 |
| Negative Control | 10.00 | 68.40 | 0 | 3.00 | 10.10 | 5.00 | 3.50 | 0 | 0 | 0 | 0 |
| Neg Cont-Solvent | 31.65 | 0 | 0 | 9.49 | 31.96 | 15.82 | 11.08 | 0 | 0 | 0 | 0 |

In Table 3 is demonstrated the ZOI results for the sustained release of the antimicrobial film-forming polymer composition for dried Sample 5a as a function of time (for a period of 72 hr) against the opportunistic pathogens of Streptococcus pyogenes, Escherichia coli, and Vibrio vulnificus. Sample 5a was composed of the TRIS:HEMA polymer with incorporated PHMB, GML, DER, and Sensiva SC10. The negative control (TRIS:HEMA) had no antimicrobial agents and no ZOI data was obtained. All results were acquired following the evaporation of ethanol (and water) from the polymer films. For these opportunistic bacteria, antimicrobial behavior is noted over several days, supporting a sustained release of the antimicrobial components from the film-forming polymer with other additives in the various aqueous broths studied.

Using dried Sample 7a, with a PHMB content of 1.21 wt-% and a GML content of 0.50 wt-%, the Log Reduction data of this antimicrobial sunscreen composition was studied against Candida albicans, Vibrio vulnificus, Pseudomonas aeruginosa, Staphylococcus aureus, and Streptococcus pyogenes for a period of 48 hours (Table 5). The negative control was the dried TRIS:HEMA polymer containing the four sunscreen agents (Neg Cont-Solvent), which had no activity against any of these microorganisms, even though HMS (homosalate) and OCTS (octisalate) are salicylic acid derivatives with available phenol groups. Within 48 hours, the Log Reductions ranged from a 4-Log Reduction for Vibrio vulnificus to an 8-Log Reduction for Streptococcus pyogenes, two of the most prominent opportunistic pathogens causing necrotizing fasciitis, in addition to being highly active against Pseudomonas aeruginosa, Staphylococcus aureus, and *Candida albicans*. Table 5 demonstrates that a water-insoluble polymer coating containing sunscreen additives and antimicrobial agents, in the presence of a surfactant and an antimicrobial emollient, is highly biocidal against pathogenic microorganisms.

TABLE 5

Antimicrobial Sunscreen Log Reduction for *C. albicans*, *V. vulnificus*, *P. aeruginosa*, *S. aureus*, and *S. pyogenes*

| | Log Reduction 48 hr | | | | |
|---|---|---|---|---|---|
| Sample | C. albicans | V. vulnificus | P. aeruginosa | S. aureus | S. pyogenes |
| 7a | 5 | 4 | 8 | 5 | 8 |

In order to determine the individual biocidal activity of PHMB and other antimicrobial agents, including GML (glycerol monolaurate), CDA (chlorhexidine diacetate), ALEX (alexidine dihydrochloride), and BZT (benzethonium chloride), each with Sensiva SC10 and four sunscreen agents, in Table 6 are presented various antimicrobial sunscreen formulations, either in solution (Samples 8, 9, 10, 11, 12, 13) or their respective compositions dried of solvent (Samples 8a, 9a, 10a, 11a, 12a, 13a). Samples 8 and 8a additionally contain only PHMB, while Samples 9 and 9a contain PHMB and CDA (chlorhexidine diacetate), Samples 10 and 10a contain PHMB and BZT (benzethonium chloride), Sample 11 and 11a contain PHMB and ALEX (alexidine dihydrochloride), Samples 12 and 12a contain PHMB with CDA and BZT, and Samples 13 and 13a contain PHMB and GML (glycerol monolaurate).

(GML), were highly effective, with Sample 13a increasing its antimicrobial behavior over time. Alexidine is a bis (biguanide) compound, similar to PHMB, poly(hexamethylene biguanide), although of lower molecular weight by being a dimeric biguanide as opposed to a low molecular weight polymeric biguanide. The alexidine composition (Sample 11a) was also more effective than the chlorhexidine composition (Sample 9a), even though the chlorhexidine concentration was over 50 times greater. Glycerol monolaurate is a hydrophobic monoacyl glycerol, with noted antimicrobial activity against Gram-positive bacteria and not Gram-negative bacteria. Surprisingly, glycerol monolaurate in combination with PHMB were the most highly effective antimicrobial agents against Gram-negative *Vibrio vulnificus*, and substantially more effective than PHMB with Sensiva SC10. Glycerol monolaurate, in combination with PHMB (Sample 13a), had the largest ZOI at 96 hours.

TABLE 7

Sustained Release ZOI for Films of Antimicrobial Sunscreen Polymer Compositions

| | ZOI *V. vulnificus* (cm$^2$) | |
|---|---|---|
| Sample | 24 hr | 96 hr |
| 8a | 0.50 | 0.70 |
| 9a | 0.80 | 0.80 |
| 10a | 0.80 | 0.80 |
| 11a | 1.30 | 1.10 |
| 12a | 0.90 | 0.90 |
| 13a | 1.10 | 1.50 |

TABLE 6

Antimicrobial Sunscreen Polymer Compositions, Solutions and Dried Films

| | Compositions, wt % | | | | | | | | | | | | |
|---|---|---|---|---|---|---|---|---|---|---|---|---|---|
| Sample | T:H 2.5:1 | EtOH | Water | AVO | HMS | OCTS | OCTO | PHMB | GML | CDA | ALEX | BZT | SC10 |
| 8 | 10.00 | 65.58 | 1.52 | 3.10 | 10.40 | 5.10 | 3.60 | 0.38 | 0 | 0 | 0 | 0 | 0.32 |
| 8a | 30.40 | 0.00 | 0.00 | 9.42 | 31.61 | 15.50 | 10.94 | 1.16 | 0 | 0 | 0 | 0 | 0.97 |
| 9 | 9.90 | 64.28 | 1.49 | 3.10 | 9.90 | 5.00 | 3.70 | 0.37 | 0 | 1.90 | 0 | 0 | 0.36 |
| 9a | 28.92 | 0.00 | 0.00 | 9.06 | 28.92 | 14.61 | 10.81 | 1.08 | 0 | 5.55 | 0 | 0 | 1.05 |
| 10 | 9.90 | 65.87 | 1.65 | 3.50 | 9.60 | 4.90 | 3.60 | 0.41 | 0 | 0 | 0 | 0.25 | 0.32 |
| 10a | 30.48 | 0.00 | 0.00 | 10.78 | 29.56 | 15.09 | 11.08 | 1.26 | 0 | 0 | 0 | 0.77 | 0.98 |
| 11 | 9.80 | 65.24 | 1.54 | 3.70 | 10.50 | 5.10 | 3.40 | 0.38 | 0 | 0 | 0.035 | 0 | 0.30 |
| 11a | 29.51 | 0.00 | 0.00 | 11.14 | 31.62 | 15.35 | 10.23 | 1.14 | 0 | 0 | 0.11 | 0 | 0.90 |
| 12 | 10.00 | 63.56 | 1.66 | 3.10 | 10.30 | 4.80 | 3.50 | 0.41 | 0 | 2.07 | 0 | 0.25 | 0.35 |
| 12a | 28.75 | 0.00 | 0.00 | 8.91 | 29.62 | 13.80 | 10.06 | 1.18 | 0 | 5.95 | 0 | 0.72 | 1.01 |
| 13 | 9.80 | 65.06 | 1.63 | 3.60 | 10.60 | 4.90 | 3.50 | 0.41 | 0.20 | 0 | 0 | 0 | 0.30 |
| 13a | 29.42 | 0.00 | 0.00 | 10.81 | 31.82 | 14.71 | 10.51 | 1.23 | 0.60 | 0 | 0 | 0 | 0.90 |

The dried polymers (Samples 8a, 9a, 10a, 11a, 12a, 13a) were studied for ZOI against *Vibrio vulnificus* (Table 7) for 24 hours and 96 hours. It is seen that Sample 8a, which contained only with PHMB and sunscreen agents, while being antimicrobial displaying sustained release properties, was the least effective of the formulations studied, indicating that Sensiva SC10, with its antimicrobial capryl glycol (1,2-octanediol) component, active against certain deodorant-based Gram-positive bacteria, provided little substantive assistance in this biocidal behavior. For the other antimicrobial compositions, Sample 11a, with alexidine dihydrochloride (ALEX), and Sample 13a, with glycerol monolaurate In Table 8 is presented an antimicrobial formulation of PHMB and GML with DER and SC10 with the four sunscreen additives of AVO, HMS, OCTS, and OCTO in denatured ethanol (Sample 14). Sample 14a is obtained from drying Sample 14. Sample 5 is related to Sample 14 but does not include the sunscreen agents. Although the PHMB and GML concentrations of the two solutions of Samples 5 and 14 are similar, after solvent evaporation Sample 5a is considerably higher in antimicrobial content than Sample 14a because of the lack of sunscreen additives.

TABLE 8

Antimicrobial Solution and Film, with Sunscreen Additives

| | Compositions, wt % | | | | | | | | | | |
|---|---|---|---|---|---|---|---|---|---|---|---|
| Sample | T:H 2.5:1 | EtOH | Water | AVO | HMS | OCTS | OCTO | PHMB | GML | DER | SC10 |
| 14 | 9.13 | 68.23 | 1.75 | 2.82 | 9.08 | 4.51 | 3.17 | 0.39 | 0.52 | 0.08 | 0.32 |
| 14a | 30.41 | 0 | 0 | 9.39 | 30.25 | 15.02 | 10.56 | 1.30 | 1.73 | 0.27 | 1.07 |

In Table 9 are presented the zones of inhibition of dried Samples 5a and 14a, pertaining to an antimicrobial polymer composition without sunscreen additives (Sample 5a) and with sunscreen additives (Sample 14a). The ZOI sustained release data obtained over a 72 hour period for *Streptococcus pyogenes*, *Escherichia coli*, and *Vibrio vulnificus* was similar for both Samples, with a slight preference to Sample 14a with *Vibrio vulnificus*, possibly due to its lower amount of polymer coating and greater ease of antimicrobial diffusion from the polymer coating. The added sunscreen agents have either no effect or a minimal effect on antimicrobial behavior.

TABLE 9

ZOI Comparison of Antimicrobial Compositions, with and without Sunscreen Additives

| | ZOI *S. pyogenes* (cm$^2$) | | | ZOI *E. coli* (cm$^2$) | | | ZOI *V. vulnificus* (cm$^2$) | | |
|---|---|---|---|---|---|---|---|---|---|
| Sample | 24 hr | 48 hr | 72 hr | 24 hr | 48 hr | 72 hr | 24 hr | 48 hr | 72 hr |
| 5a | 0.65 | 0.65 | 0.58 | 0.21 | 0.21 | 0.26 | 0.45 | 0.55 | 0.65 |
| 14a | 0.65 | 0.65 | 0.58 | 0.47 | 0.17 | 0.21 | 0.69 | 0.75 | 0.82 |

The utilization of an antimicrobial agent in combination with an insect repellent, wherein the insect repellent is released based upon its vapor pressure emanating from the polymer coating, is an important adjunct to preventing ingress to a human or animal host of microorganisms originating from a bite, sting, puncture, etc., from the generation of an open wound. In Table 10 is presented a solution composition based upon the Acrylate Copolymer of octylacrylamide/acrylates/butylaminoethyl methacrylate from MakingCosmetics Inc. (Sample 15) in a denatured ethanol/water with the antimicrobial agents of PHMB and GML admixed with the insect repellent OLE (Oil of Lemon Eucalyptus, Citriodiole, Citrifine International). The OLE utilized is a commercial product (Citriodiole) that typically contains 64% p-menthane-3,8-diol, which consists of a mixture of racemic cis and trans isomers, with two other minor related racemic isomers. When Sample 15 is cast with solvent evaporation, the polymer film (Sample 15a) obtained was slightly translucent, non-tacky, pin-hole free, and homogeneous to the eye.

TABLE 10

| Polymer Solution and Film with OLE Insect Repellent | | | | | | |
|---|---|---|---|---|---|---|
| | Composition, wt % | | | | | |
| Sample | ACR | EtOH | Water | PHMB | GML | OLE |
| 15 | 10.00 | 84.54 | 2.00 | 0.46 | 0.50 | 2.50 |
| 15a | 74.29 | 0 | 0 | 3.42 | 3.72 | 18.57 |

In Table 11 are shown solution and dried compositions of the film-forming ACR polymer with the antimicrobial agents of PHMB and GML (Samples 16, 16a) with and without the sunscreen additives of AVO, HMS, OCTS, OCTO (Samples 17, 17a), and with and without the insect repellent OLE (Samples 18, 18a). Films of Samples 16a and 17a cast on glass slides were homogeneous, pin-hole free, mildly translucent, and non-tacky, while that incorporating OLE (Sample 18a) was similar but had a slight tack.

TABLE 11

| Sunscreen Insect Repellent with Antimicrobial Agents | | | | | | | | | | |
|---|---|---|---|---|---|---|---|---|---|---|
| | Composition, wt % | | | | | | | | | |
| Sample | ACR | EtOH | Water | AVO | HMS | OCTS | OCTO | PHMB | GML | OLE |
| 16 | 10.00 | 87.04 | 2.00 | 0 | 0 | 0 | 0 | 0.46 | 0.50 | 0 |
| 16a | 91.24 | 0 | 0 | 0 | 0 | 0 | 0 | 4.20 | 4.56 | 0 |
| 17 | 9.78 | 66.46 | 1.80 | 2.93 | 9.78 | 4.89 | 3.42 | 0.45 | 0.49 | 0 |
| 17a | 30.81 | 0 | 0 | 9.23 | 30.81 | 15.41 | 10.78 | 1.42 | 1.54 | 0 |
| 18 | 9.54 | 64.88 | 1.76 | 2.86 | 9.54 | 4.77 | 3.34 | 0.44 | 0.48 | 2.39 |
| 18a | 28.60 | 0 | 0 | 8.57 | 28.60 | 14.3 | 10.01 | 1.32 | 1.44 | 7.16 |

The invention claimed is:

1. A method of killing *Vibrio vulnificus* on a biological surface, comprising:
   applying a liquid antimicrobial, water-insoluble, polymer formulation to the biological surface, said liquid antimicrobial, water-insoluble, polymer formulation comprising:
      0.10 to 50.0 wt-% of a water-insoluble polymer dissolved in about 45.0 to 99.7 wt-% of a volatile polar and/or nonpolar liquid,
      0.30 wt-% to 1.0 wt-% poly(hexamethylene biguanide), one or more salts of poly(hexamethylene biguanide), or combinations thereof, and
      an antimicrobial composition comprising 0.20 wt-% to 4.0 wt-% of glycerol monolaurate;
      wherein all weight percentages are based on the total weight of the antimicrobial, water-insoluble, polymer coating formulation; and
   evaporating said volatile polar and/or nonpolar liquid from the biological surface to obtain a polymer coating thereon;
   wherein the polymer coating formed by said evaporating provides a log reduction of at least 2 log orders at 48 hours against *Vibrio vulnificus*.

2. The method according to claim 1, wherein said applying step comprises application by at least one method selected from the group consisting of spraying, wiping, dipping, painting, brushing, casting, and aerosolization.

3. The method according to claim 1, wherein the antimicrobial composition is present in an amount of up to 10.00 wt-%, and the antimicrobial composition further comprises one or more antimicrobial agents selected from the group consisting of alexidine, a salt of alexidine, chlorhexidine, a salt of chlorhexidine, and benzethonium chloride.

4. The method according to claim 1, wherein the antimicrobial composition further comprises a monoacyl glycerol selected from the group consisting of 1-O-decanoylglycerol, monocaprin, 1-O-undecanoylglycerol, 1-O-undecenoylglycerol, 1-O-tridecanoylglycerol, 1-O-tetradecanoylglycerol, monomyristin, 1-O-pentadecanoylglycerol, 1-O-hexadecanoylglycerol, 1-O-heptadecanoylglycerol, 1-O-octanoylglycerol, monocaprylin, and combinations thereof.

5. The method according to claim 1, wherein the antimicrobial composition further comprises one or more antimicrobial agents selected from the group consisting of alexidine, a salt of alexidine and combinations thereof.

6. The method according to claim 1, wherein the antimicrobial composition further comprises at least one additional additive selected from the group consisting of surfactants, sunscreen agents, insect repelling agents, emollients, active pharmaceutical agents, antibiotics, essential oils, polymer film flexibilizers, plasticizers, compatibilizers, skin care additives, and combinations thereof.

7. The method according to claim 1, wherein the antimicrobial composition further comprises a surfactant selected from the group consisting of poloxamers, poloxamines, polyethylene glycol esters of fatty acids, polyoxyethylene or polyoxypropylene ethers of $C_{12}$-$C_{18}$ higher alkanes polysorbate 20, polysorbate 80, polyoxyethylene propylene glycol stearate, nonylphenol ethoxylates, cocoamidopropyl betaine, decyl glucoside, lauryl glucoside, sodium N-lauryl-B-iminodipropionate, sodium lauriminodipropionate, disodium lauriminodipropionate, disodium 3,3'-(dodecylimino) dipropanoate, disodium 3-[2-carboxylatoethyl(dodecyl) amino]propanoate, disodium lauroamphodiacetate, sodium-2-ethylhexyliminodipropionate, disodium cocoamphodiacetate, sodium cocoamphoacetate, ammonium lauriminodipropionate, triethanolamine lauraminopropionate, disodium cocaminodipropionate, cocamidopropyl betaine, lauramidopropyl betaine, cocobetaine, laurylbetaine, isostearamidopropyl betaine, cocamidopropyl hydroxysultaine, lauramidopropyl hydroxysultaine, disodium capryloamphodiacetate, sodium lauroamphoacetate, sodium cocaminodipropionate, ammonium cocaminodipropionate, triethanolamine lauriminodipropionate, sodium cocoamphohydroxypropylsulfonate, sodium cocoamphopropionate, sodium cornamphopropionate, sodium lauroamphohydroxypropylsulfonate, sodium lauroamphopropionate, ammonium cocaminopropionate, ammonium cocoamphoacetate, disodium caproamphodiacetate, disodium caproamphoadipropionate, disodium capryloamphodiacetate, disodium capryloamphodipriopionate, disodium cocoamphocarboxyethylhydroxypropylsulfonate, disodium laureth-5 carboxyamphodiacetate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, cocoamidopropyldimethylglycine, cocoamphocarboxypropionate, cocamidopropyl PG-dimonium chloride phosphate, oleamidopropyl betaine, myristamidopropyl betaine, dimethicone propyl PG-betaine, palmitamidopropyl betaine, undecylenamidopropyl betaine, and combinations thereof.

8. The method according to claim 1, wherein the antimicrobial composition further comprises a sunscreen agent selected from the group consisting of avobenzone (butylmethoxydibenzoylmethane; 4-tert-butyl-4'-methoxydibenzoylmethane), homosalate (homomenthyl salicylate; 3,3,5-trimethylcyclohexyl 2-hydroxybenzoate), octisalate (octyl salicylate; 2-ethylhexyl salicylate; 2-ethylhexyl 2-hydroxybenzoate), octocrylene (2- ethylhexyl-2-cyano-3,3-diphenyl-2-acrylate; 2-ethylhexyl-2-cyano-3,3-diphenyl-2- propenoate), oxybenzone (benzophenone-3; (2-hydroxy-4-methoxyphenyl)phenylmethanone; 2-hydroxy-4-methoxybenzophenone), otinoxate (ethylhexyl methoxycinnamate; octyl methoxycinnamate), zinc oxide, titanium dioxide, and combinations thereof.

9. The method according to claim 1, wherein the antimicrobial composition further comprises an insect repelling agent selected from the group consisting of oil of lemon eucalyptus, p-menthane-3,8-diol, picaridin, icaridin, lemongrass oil, citronella oil, castor oil, cedar oil, clove oil, geraniol oil, peppermint oil, eucalyptus oil, pine oil, rosemary oil, cedarwood oil, lavender oil, spearmint oil, lime oil, bog myrtle, neem oil, soybean oil, N,N-diethyltoluatnide, and combinations thereof.

10. The method according to claim 1, wherein the liquid antimicrobial, water-insoluble, polymer formulation further comprises a film-forming polymer selected from the group consisting of acrylate polymers, methacrylate polymers, siloxanyl polymers, dimethicones, acrylamide polymers, octylacrylamide polymers, vinyl acetate polymers, N-vinylpyrollidone polymers, maleate polymers, crotonate polymers, alkene polymers, styrene polymers, butadiene polymers, vinyl methyl ether polymers, vinyl proprionate polymers, urethane polymers, polyesters, quaternary ammonium polymers, N-vinylcaprolactam polymers, and combinations thereof.

11. The method according to claim 1, wherein the liquid. antimicrobial, water-insoluble, polymer formulation further comprises an aerosol propellant selected from the group consisting of ethane, propane, n-butane, isobutane, 1,1,1,2-tetrafluoroethane, 1,1,1,2,3,3,3-heptafluoropropane, dimethyl ether, methyl ethyl ether, compressed gases selected from the group consisting of nitrogen, nitrous oxide, air, and carbon dioxide, and combinations thereof.

12. The method according to claim 1, wherein the liquid antimicrobial, water-insoluble, polymer formulation further comprises 0.10 wt-% to 4.0 wt-% of solubilized water as part of the volatile polar and/or nonpolar liquid.

13. The method according to claim 1, wherein the liquid antimicrobial, water-insoluble, polymer formulation is non-aqueous.

14. The method according to claim 1, wherein the biological surface is skin, tissue, or mucous membrane.

15. A method of treating or limiting growth of *Vibrio vulnficus* comprising:
administering a liquid antimicrobial polymer composition to a subject to form an antimicrobial, water-insoluble, polymer coating,
wherein the antimicrobial, water-insoluble, polymer coating comprises: poly(hexamethylene biguanide), one or more salts of poly(hexamethylene biguanide), or combinations thereof in an amount from at least 1.0 wt-% to 10.00 wt-%,
an antimicrobial composition comprising 0.60 wt-% to 10.00 wt-% of glycerol monolaurate, and
up to 98.4 wt-% of a water-insoluble, polymer,
wherein all weight percentages are based on the total weight of the antimicrobial, water-insoluble, polymer coating composition;
wherein said antimicrobial, water-insoluble, polymer coating provides a log reduction of at least 2 log orders at 48 hours against the *Vibrio vulnficus*.

16. A method of limiting the growth of *Vibrio vulnficus* on a biological surface, comprising:
administering a liquid antimicrobial, water-insoluble, polymer composition to the biological surface to form an antimicrobial, water-insoluble, polymer coating,
wherein the liquid antimicrobial, water-insoluble, polymer composition comprises: 45.0 to 99.4 wt-% of a volatile polar and/or nonpolar liquid;
0.10 to 50.0 wt-% of a water-insoluble polymer dissolved in said volatile polar and/or nonpolar liquid;
0.30 wt-% to 1.0 wt-% poly(hexamethylene biguanide), one or more salts of poly(hexamethylene biguanide), or combinations thereof, and
an antimicrobial composition comprising 0.20 wt-% to 4.0 wt-% of glycerol monolaurate,
wherein all weight percentages are based on the total weight of the liquid antimicrobial, water-insoluble, polymer composition;
wherein a polymer coating formed from said liquid, antimicrobial, water-insoluble, polymer composition provides a log reduction of at least 2 log orders at 48 hours against the *Vibrio vulnficus*.

17. The method according to claim 1, wherein said applying step comprises mitigating an infection caused by the *Vibrio vulnficus*.

18. The method according to claim 1, wherein the antimicrobial composition is present in an amount of up to 10.00 wt-%, and the antimicrobial composition further comprises
one or more antimicrobial agents selected from the group consisting of alexidine, a salt of alexidine, and combinations thereof.

19. The method according to claim 15, wherein the antimicrobial composition is present in an amount of up to 10.00 wt-%, and the antimicrobial composition further comprises
one or more antimicrobial agents selected from the group consisting of alexidine, a salt of alexidine, and combinations thereof.

20. The method according to claim 16, wherein the antimicrobial composition is present in an amount of up to 10.00 wt-%, and the antimicrobial composition further comprises
one or more antimicrobial agents selected from the group consisting of alexidine, a salt of alexidine, and combinations thereof.

* * * * *